United States Patent
Jazayeri-Dezfuly et al.

(10) Patent No.: US 10,174,101 B2
(45) Date of Patent: Jan. 8, 2019

(54) STABLE PROTEINS

(75) Inventors: Seyed Ali Jazayeri-Dezfuly, Hertfordshire (GB); Fiona Hamilton Marshall, Hertfordshire (GB)

(73) Assignee: Heptares Therapeutics Limited, Hertfordshire (GB)

( * ) Notice: Subject to any disclaimer, the term of this patent is extended or adjusted under 35 U.S.C. 154(b) by 0 days.

(21) Appl. No.: 14/237,678

(22) PCT Filed: Aug. 9, 2012

(86) PCT No.: PCT/GB2012/051940
§ 371 (c)(1),
(2), (4) Date: May 19, 2014

(87) PCT Pub. No.: WO2013/021206
PCT Pub. Date: Feb. 14, 2013

(65) Prior Publication Data
US 2014/0315299 A1    Oct. 23, 2014

Related U.S. Application Data

(60) Provisional application No. 61/522,147, filed on Aug. 10, 2011.

(51) Int. Cl.
| | | |
|---|---|---|
| C07K 14/72 | (2006.01) | |
| C07K 14/705 | (2006.01) | |
| A61K 38/54 | (2006.01) | |
| G01N 33/566 | (2006.01) | |
| C12N 9/36 | (2006.01) | |

(52) U.S. Cl.
CPC .......... *C07K 14/723* (2013.01); *C07K 14/705* (2013.01); *C12N 9/2462* (2013.01); *G01N 33/566* (2013.01); *C07K 2319/00* (2013.01); *C07K 2319/60* (2013.01)

(58) Field of Classification Search
CPC ............ C12N 15/1136; C12N 15/1138; C07K 14/4722
USPC ....... 435/69.1, 69.7; 424/144.1, 138.1, 143.1
See application file for complete search history.

(56) References Cited

U.S. PATENT DOCUMENTS

| | | | |
|---|---|---|---|
| 6,692,696 | B1 | 2/2004 | Alberte |
| 7,294,472 | B2 | 11/2007 | Gilchrist et al. |
| 7,998,694 | B2 | 8/2011 | Trinquet et al. |
| 8,470,561 | B2 | 6/2013 | Kobilka |
| 8,703,915 | B2 | 4/2014 | Jazayeri-Dezfuly et al. |
| 8,748,182 | B2 | 6/2014 | Heal et al. |
| 8,785,135 | B2 | 7/2014 | Henderson et al. |
| 8,790,933 | B2 | 7/2014 | Weir et al. |
| 8,900,591 | B2 | 12/2014 | Hutchings et al. |
| 9,081,020 | B2 | 7/2015 | Weir et al. |
| 9,260,505 | B2 | 2/2016 | Weir et al. |
| 2010/0190188 | A1 | 7/2010 | Henderson et al. |
| 2011/0027910 | A1 | 2/2011 | Weir et al. |
| 2011/0028700 | A1 | 2/2011 | Heal |
| 2011/0031438 | A1 | 2/2011 | Stevens et al. |
| 2011/0046351 | A1 | 2/2011 | Weir et al. |
| 2011/0112037 | A1 | 5/2011 | Warne et al. |
| 2012/0165507 | A1 | 6/2012 | Jazayeri-Dezfuly et al. |
| 2012/0270230 | A1 | 10/2012 | Henderson et al. |
| 2012/0288913 | A1 | 11/2012 | Hanson et al. |
| 2013/0224238 | A1 | 8/2013 | Hutchings et al. |
| 2014/0031525 | A1 | 1/2014 | Robertson et al. |
| 2014/0315299 | A1 | 10/2014 | Jazayeri-Dezful et al. |
| 2014/0357521 | A1 | 12/2014 | Steyaert et al. |
| 2015/0147822 | A1 | 5/2015 | Marshall et al. |
| 2015/0261911 | A1 | 9/2015 | Bortolato et al. |
| 2016/0052991 | A1 | 2/2016 | Henderson et al. |
| 2016/0327576 | A1 | 11/2016 | Weir et al. |
| 2017/0145075 | A1 | 5/2017 | Robertson et al. |
| 2018/0086814 | A1 | 3/2018 | Henderson et al. |

FOREIGN PATENT DOCUMENTS

| | | |
|---|---|---|
| EP | 1491207 A1 | 12/2004 |
| JP | 2002-510790 | 4/2002 |
| JP | 2004-238384 A | 8/2004 |
| JP | 2005-503124 A | 2/2005 |
| JP | 2005-515402 | 5/2005 |
| JP | 2006-506642 | 2/2006 |
| JP | 2006-340717 A | 12/2006 |
| JP | 2007-530919 | 11/2007 |
| JP | 2009-506336 A | 2/2009 |
| JP | 2011-224018 A | 11/2011 |
| WO | WO 2000/070343 | 11/2000 |
| WO | WO 01/58916 A2 | 8/2001 |
| WO | WO 02/29050 A2 | 4/2002 |
| WO | WO 02/083736 A2 | 10/2002 |
| WO | WO 2008/114020 A2 | 9/2008 |
| WO | WO 2009/051769 A1 | 4/2009 |
| WO | WO 2009/055512 A2 | 4/2009 |
| WO | WO 2009/081136 A2 | 7/2009 |
| WO | WO 2009/101383 A1 | 8/2009 |
| WO | WO 2009/114020 A1 | 9/2009 |
| WO | WO 2012/030735 A1 | 3/2012 |

OTHER PUBLICATIONS

[No Author Listed] Heptares Announces Publication in Nature of First Structure of Metabotropic Glutamate Receptor 5 Transmembrane Domain. Jul. 7, 2014. Last accessed at http://www.heptares.com/news/210/74/Heptares-Announces-Publication-In-Nature-Of-First-Structure-Of-Metabotropic-Glutamate-Receptor-5-Transmembrane-Domain.html on Jul. 31, 2014.

(Continued)

*Primary Examiner* — Robert B Mondesi
*Assistant Examiner* — Mohammad Y Meah
(74) *Attorney, Agent, or Firm* — Wolf, Greenfield & Sacks, P.C.

(57) ABSTRACT

The invention provides a fusion protein comprising, from N-terminus to C-terminus: a) a first portion of a Family B G-protein coupled receptor (GPCR) that comprises transmembrane helix (TM)-1, TM2 and TM3 of the GPCR; b) a stable protein domain; and c) a second portion of the GPCR comprising TM4, TM5, TM6 and TM7 of the GPCR. The invention also provides a method of crystallizing a GPCR comprising providing the fusion protein of the invention and crystallizing it to obtain crystals.

21 Claims, 14 Drawing Sheets

Figure 2:
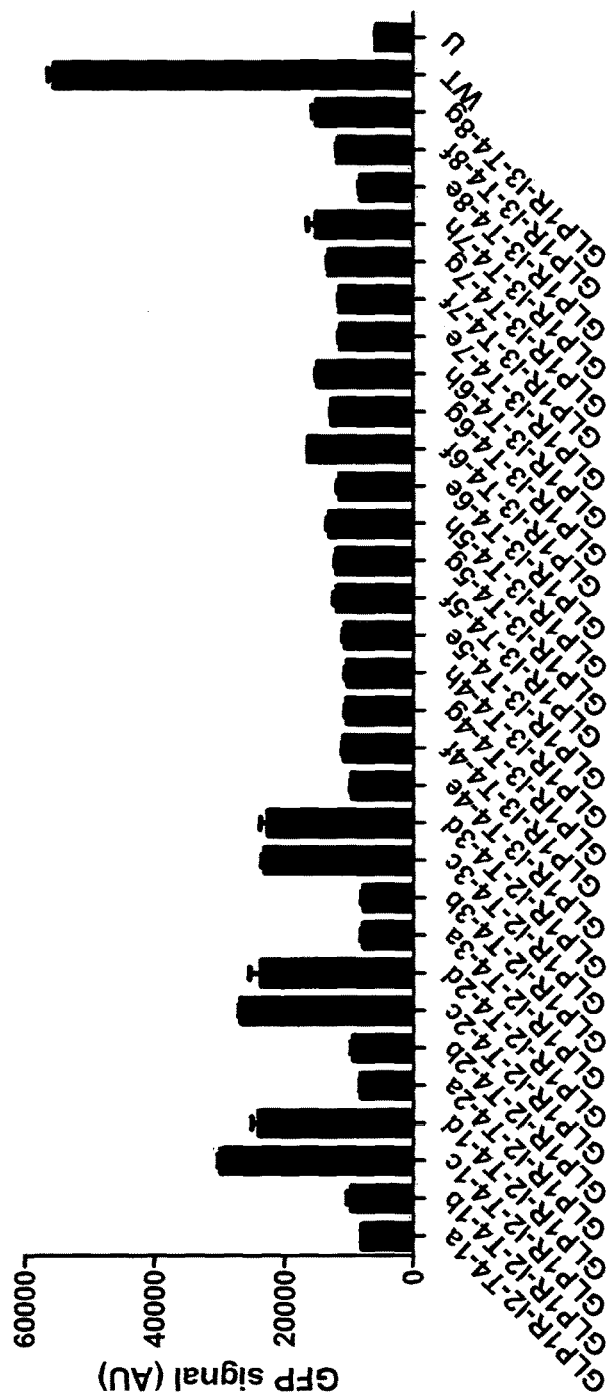

Specification includes a Sequence Listing.

(56) References Cited

OTHER PUBLICATIONS

Altschul et al., Gapped BLAST and PSI-BLAST: a new generation of protein database search programs. Nucl Acids Res. 1997 25:3389-3402.
Bill et al., Overcoming barriers to membrane protein structure determination. Nat Biotechnol. Apr. 2011;29(4):335-40. doi: 10.1038/nbt.1833.
Bockaert et al., GPCR-GIP networks: a first step in the discovery of new therapeutic drugs? Curr Opin Drug Discov and Dev. 2004. 7:649-657.
Chien et al., Structure of the human dopamine D3 receptor in complex with a D2/D3 selective antagonist. Science. Nov. 19, 2010;330(6007):1091-5. doi: 10.1126/science.1197410.
Eddy et al., Maximum Discrimination Hidden Markov Models of Sequence Consensus. J. Comput Biol. 1995. 2(1):9-23.
Engel et al., Insertion of carrier proteins into hydrophilic loops of the *Escherichia coli* lactose permease. Biochim Biophys Acta. Aug. 19, 2002;1564(1):38-46.
Flanagan, A GPCR that is not "DRY". Mol Pharmacol. Jul. 2005;68(1):1-3. Epub Apr. 26, 2005.
Foord et al., International Union of Pharmacology. XLVI. G Protein-Coupled Receptor List. Pharmacol. Rev. 2005. 57:279-288.
Frimurer et al., Structure of the integral membrane domain of the GLP1 receptor. Proteins. Jun. 1, 1999;35(4):375-86.
Harikumar et al., Molecular basis of association of receptor activity-modifying protein 3 with the family B G protein-coupled secretin receptor. Biochemistry. Dec. 15, 2009;48(49):11773-85. doi: 10.1021/bi901326k.
Jaakola et al., the 2.6 Å Crystal Structure of a Human A2A Adenosine Receptor Bound to an Antagonist. Science. Nov. 21, 2008; 322:1211-1217.
Kawate et al., Fluorescence-detection size-exclusion chromatography for precrystallization screening of integral membrane proteins. Structure. Apr. 2006;14(4):673-81.
Kenakin, Protean agonists. Keys to active receptor states? Ann. N.Y. Acad. Sci. 1997. 812:116-125.
Kobilka et al., Chimeric alpha 2-,beta 2-adrenergic receptors: delineation of domains involved in effector coupling and ligand binding specificity. Science. Jun. 3, 1988;240(4857):1310-6.
Kristiansen, Molecular mechanisms of ligand binding, signalling, and regulation within the superfamily of G-protein-coupled receptors: molecular modelling and mutagenesis approaches to receptor structure and function. Pharmacology and therapeutics. 2004. 103:21-80.
Kyte et al., A Simple Method for Displaying the Hydropathic Character of a Protein. J. Mol. Biol. 1982. 157:105-132.
Magnani et al., Co-evolving stability and conformational homogeneity of the human adenosine A2a receptor. PNAS. 2008. 105(31):10744-10749.
Neubig et al., International Union of Pharmacology Committee on Receptor Nomenclature and Drug Classification. XXXVIII. Update on Terms and Symbols in Quantitative Pharmacology. Pharmacol. Rev. 2003. 55:597-606.
Overington et al., How many drug targets are there? Natur Rev. Drug Discovery. 2006. 5:993-996.
Parthier et al., Passing the baton in class B GPCRs: peptide hormone activation via helix induction? Trends Biochem Sci. Jun. 2009;34(6):303-10. doi: 10.1016/j.tibs.2009.02.004. Epub May 14, 2009.
Rosenbaum et al., GPCR Engineering Yields High-Resolution Structural Insights into b2-Adrenergic Receptor Function. Science. 2007. 318:1266-1273.
Serrano-Vega et al., Conformational thermostabilization of the β1-adrenergic receptor in a detergent-resistant form. PNAS. 2008 105(3):877-882.
Shibata et al. Thermostabilization of the Neurotensin Receptor NTS1, J. Mol. Biol. Jul. 10, 2009; 390(2):262-277.
Thompson et al., Clustal W: improving the sensitivity of progressive multiple sequence alignment through sequence weighting, position-specific gap penalties and weight matrix choice Nucl. Acids Res. 1994. 22:4673-4680.
Kroon-Batenburg et al., Experiences with making diffraction image data available: what metadata do we need to archive? Acta Crystallogr D Biol Crystallogr. Oct. 2014;70(Pt 10):2502-9. doi: 10.1107/S1399004713029817. Epub Sep. 30, 2014.
Wiencek, New strategies for protein crystal growth. Annu Rev Biomed Eng. 1999;1:505-34.
[No Author Listed] Uniprot Database Accession No. P43220. 1995.
Ault et al., Creation of GPCR-based chemical sensors by directed evolution in yeast. Protein Eng Des Sel. Jan. 2006;19(1):1-8.
Dore et al., Structure of class C GPCR metabotropic glutamate receptor 5 transmembrane domain. Nature. Jul. 31, 2014;511(7511):557-62. doi: 10.1038/nature13396. Epub Jul. 6, 2014.
Hollenstein et al., Structure of class B GPCR corticotropin-releasing factor receptor 1. Nature. Jul. 25, 2013;499(7459):438-43. doi: 10.1038/nature12357. Epub Jul. 17, 2013.
Jazayeri et al., Extra-helical binding site of a glucagon receptor antagonist. Nature. Apr. 25, 2016;533(7602):274-7. doi: 10.1038/nature17414.
Kinoshita, [Application and development of structure-based drug design using X-ray analysis]. Nihon Yakurigaku Zasshi. Mar. 2007;129(3):186-90.
Cherezov et al., High Resolution Crystal Structure of an Engineered Human β2-Adrenergic G protein-Coupled Receptor. Science. 2007;318(5854):1258-1265. Epub Oct. 25, 2007.
Chun et al., Fusion Partner Toolchest for the Stabilization and Crystallization of G Protein-Coupled Receptors. Structure. Jun. 2012;20(6):967-76.
Heydenreich et al., Stabilization of G protein-coupled receptors by point mutations. Front Pharmacol. Apr. 20, 2015;6:82. doi: 10.3389/fphar.2015.00082. eCollection 2015.
Liu (ed), Cell Information and Regulation. China Union Medical University Press, Nov. 2003, pp. 188-189.
Liu et al., Structural Basis for Allosteric Regulation of GPCRs by Sodium Ions. Science. Jul. 2012;337(6091):232-6.
Mathew et al., Functional fusions of T4 lysozyme in the third intracellular loop of a G protein-coupled receptor identified by a random screening approach in yeast. Protein Eng Des and Sel. Oct. 2012;26(1):59-71.
Wang (ed), Protein Engineering. Beijing Chemical Industry Press, May 2002, pp. 58-59.
Warne et al., Structure of a β1-adrenergic G protein-coupled receptor. Nature. Jul. 2008. 454:486-491.
Yu et al, Introduction to Molecular Design. Beijing Higher Education Press; Germany Springer Press; Jul. 2000, pp. 130-135.
Zhai et al, Introduction to Modern Biotechnology. Beijing Higher Education Press; Germany Springer Press; Aug. 1998, pp. 123 (paragraph 3), 127 (last paragraph), 136-140.
Zhang et al., Agonist-bound structure of the human $P2Y_{12}$ receptor. Nature. May 2014;509(7498):119-22. Author Manuscript. 26 pages.
[No Author Listed] Heptares Therapeutics press release. Jan. 23, 2015. Heptares Scientists to Receive the Malcolm Campbell Memorial Prize for 2015 in Recognition of Their Outstanding Contribution to GPCR Drug Discovery. 3 pages. Last accessed on Apr. 24, 2015 from http://www.prnewswire.com/news-releases/heptares-scientists-to-receive-the-malcolm-campbell-memorial-prize-for-2015-in-recognition-of-their-outstanding-contribution-to-gper-drug-discovery-289549371.html.
[No Author Listed] Heptares Therapeutics press release. Jul. 7, 2014. Heptares has solved structures across all major GPCR families (A, B and C) providing platforms for wide-ranging structure-based and antibody drug discovery programmes. 2 pages. Last accessed on Jul. 31, 2014 from http://www.heptares.com/news/210/74/Heptares-Announces-Publication-In-Nature-Of-First-Structure-Of-Metabotropic-Glutamate-Receptor-5-Transmembrane-Domain.html.

(56) References Cited

OTHER PUBLICATIONS

[No Author Listed] Allergan and Heptares Announce Global R&D and Commercialization Partnership for Novel Treatments in Alzheimer's and Other Neurological Disorders. Press Release; Apr. 7, 2016. Last accessed from <https://www.heptares.com/index.php?mact=News,cntnt01,print,0&cntnt01articleid=268&cntnt01showtemplate=false&cntnt01returnid=74> on May 5, 2016.

[No Author Listed] Guide to Pharmacology: G protein-coupled receptors. Last accessed from <http://www.guidetopharmacology.org/GRAC/FamilyDisplayForward?familyId=694&familyType=GPCR> on Apr. 12, 2018. 4 pages.

[No Author Listed] Heptares and Kymab enter Strategic Collaboration to Discover, Develop and Commercialise Novel Antibody Therapeutics. Press Release; Apr. 18, 2016. Last accessed from <https://www.heptares.com/index.php?mact=News,cntn101,print,0&cntnt01articleid=269&cntnt01showtemplate=false&cntnt01returnid=74> on May 5, 2016.

[No Author Listed] Heptares Awarded $5.5 Million Research & Development Grant from the US National Institute on Drug Abuse (NIDA). Press Release; Sep. 28, 2015. Last accessed from <https://www.heptares.com/index.php?mact=News,cntn101,print,0&cntnt01articleid=252&cntnt01showtemplate=false&cntnt01returnid=74> on May 5, 2016.

[No Author Listed] Heptares Enters Strategic Drug Discovery Collaboration with Pfizer Inc. focused on GPCR Targets across Multiple Therapeutics Areas. Press Release; Nov. 30, 2015. Last accessed from <https://www.heptares.com/index.php?mact=News,cntnt01,print,0&cntnt01articleid=257&cntnt01showtemplate=false&cntnt01returnid=74> on May 5, 2016.

[No Author Listed] Heptares wins Best Established Biotech Company Award at OBN Annual Awards 2016. Press Release; Oct. 7, 2016. Last accessed from <https://www.heptares.com/index.php?mact=News,cntnt01,print,0&cntnt01articleid=278&cntnt01showtemplate=false&cntnt01returnid=74> on May 31, 2017.

[No Author Listed] Teva and Heptares Enter Agreement to Discover and Develop Novel, Small-Molecule CGRP Antagonists for Treatment of Migraine. Press Release; Nov. 25, 2015. Last accessed from <https://www.heptares.com/index.php?mact=News,cntnt01,print,0&cntnt01articleid=256&cntnt01showtemplate=false&cntnt01returnid=74> on May 5, 2016.

[No Author Listed] The Nobel Prize in Chemistry 2012. Press Release; Oct. 10, 2012. Last accessed from <https://www.nobelprize.org/nobe_prizes/chemistry/laureates/2012/press.html> on Nov. 29, 2012.

Barroso, Constitutive activation of the neurotensin receptor 1 by mutation of Phe(358) in Helix seven. Br J Pharmacol. Feb. 2002;135(4):997-1002.

Boehm et al., Chemical Probe Identification Platform for Orphan GPCRs Using Focused Compound Screening: GPR39 as a Case Example. ACS Med Chem Lett. Sep. 16, 2013;4(11):1079-84. doi: 10.1021/m1400275z. eCollection Nov. 14, 2013.

Chung et al., Orphan GPCR research. Br J Pharmacol. Mar. 2008;153 Suppl 1:S339-46. Epub Dec. 10, 2007.

Garippa et al., High-throughput confocal microscopy for beta-arrestin-green fluorescent protein translocation G protein-coupled receptor assays using the Evotec Opera Methods Enzymol. 2006;414:99-120.

Hu et al., Identification of Surrogate Agonists and Antagonists for Orphan G-Protein-Coupled Receptor GPR139. J Biomol Screen. Aug. 2009;14(7):789-97.

Huang et al., Discovery of human antibodies against the C5aR target using phage display technology. J Mol Recognit. Jul.-Aug. 2005;18(4):327-33.

Jacob et al., Virtual screening of GPCRs: An in silico chemogenomics approach. BMC Bioinformatics. Sep. 6, 2008;9:363. doi: 10.1186/1471-2105-9-363.

Kitabgi et al., Functional domains of the subtype 1 neurotensin receptor (NTS1). Peptides. Oct. 2006;27(10):2461-8. Epub Aug. 9, 2006.

Klabunde et al., Chemogenomics approaches to G-protein coupled receptor lead finding. Ernst Schering Res Found Workshop. 2006;58:31-46.

Kostenis, G Proteins in Drug Screening: From Analysis of Receptor-G Protein Specificity to Manipulation of GPCR-Mediated Signaling Pathways. Curr Pharm Des. 2006;12(14):1703-15.

Kroeze et al., PRESTO-TANGO: an open-source resource for interrogation of the druggable human GPCR-ome. Nat Struct Mol Biol. May 2015;22(5):362:369. Author manuscript.

Lee et al., Cell imaging assays for G protein-coupled receptor internalization: application to high-throughput screening. Methods Enzymol. 2006;414:79-98.

Mackrill, Generation, Use, and Validation of Receptor-Selective Antibodies. Methods in Molecular Biology. 2004;259:47-65.

Miller et al., Engineering an ultra-thermostable β1-adrenoceptor. J Mol Biol. Oct. 28, 2011;413(3):1-17. Author manuscript.

Milligan et al., Chimeric Gα proteins: their potential use in drug discovery. Trends Pharmacol Sci. Mar. 1999;20(3):118-124.

Mishina et al., Multiplex GPCR Assay in Reverse Transfection Cell Microarrays. J Biomol Screen. Apr. 2004;9(3):196-207.

New et al., Chimeric and Promiscuous G Proteins in Drug Discovery and the Deorphanization of GPCRs. Drug Design Reviews—Online. 2005;2:66-79.

Ngo et al., Identifying ligands at orphan GPCRs: current status using structure-based approaches. Br J Pharmacol. Oct. 2016;173(20):2934-51. doi: 10.1111/bph.13452. Epub Mar. 5, 2016.

Robas et al., Maximizing serendipity: strategies for identifying ligands for orphan G-protein-coupled receptors. Curr Opin Pharmacol. Apr. 2003;3(2):121-6.

Shiroishi, [Strategies for the structural determination of G protein-coupled receptors: from an example of histamine $H_1$ receptor]. Yakugaku Zasshi. 2013;133(5):539-47.

Vohra et al., Similarity between class a and class B G-protein-coupled receptors exemplified through calcitonin gene-related peptide receptor modelling and mutagenesis studies J R Soc Interface. Dec. 12, 2012;10(79):20120846. doi: 10.1098/rsif.2012.0846. Print Feb. 2013.

Wang et al., Establishment of a chimeric reporting system for the universal detection and high-throughput screening of a G protein-coupled receptors. Biosens Bioelectron. Mar. 15, 2009;24(7):2298-304. doi: 10.1016/j.bios.2008.11.023. Epub Dec. 7, 2008.

Wise et al., The Identification of Ligands at Orphan G-Protein Coupled Receptors. Annu Rev Pharmacol Toxicol. 2004;44:43-66.

Zhang et al., Selection of Active ScFv to G-Protein-Coupled Receptor CCR5 Using Surface Antigen-Mimicking Peptides. Biochemistry. Oct. 5, 2004;43(39):12575-84.

Office Communication dated Oct. 1, 2014 for U.S. Appl. No. 13/493,898.

Office Communication dated Nov. 12, 2014 for U.S. Appl. No. 13/980,497.

Office Communication dated Feb. 11, 2015 for U.S. Appl. No. 14/255,939.

Office Communication dated Feb. 2, 2015 for U.S. Appl. No. 13/980,497.

U.S. Appl. No. 14/989,744, filed Jan. 6, 2016, Weir et al.

Office Communication dated Jan. 13, 2016 for U.S. Appl. No. 14/836,820.

Office Communication dated Dec. 31, 2015 for U.S. Appl. No. 13/980,497.

Office Communication dated Oct. 13, 2015 for U.S. Appl. No. 14/210,266.

U.S. Appl. No. 14/210,266, filed Mar. 14, 2014, Bortolato et al.

PCT/GB2012/051940, Feb. 1, 2013, International Search Report and Written Opinion.

Office Communication dated Feb. 14, 2012 for U.S. Appl. No. 12/450,358.

Office Communication dated Jul. 27, 2012 for U.S. Appl. No. 12/746,674.

Office Communication dated Aug. 1, 2012 for U.S. Appl. No. 12/921,036.

Office Communication dated Sep. 5, 2012 for U.S. Appl. No. 12/866,594.

(56) References Cited

OTHER PUBLICATIONS

Office Communication dated Sep. 11, 2012 for U.S. Appl. No. 12/450,358.
Office Communication dated Jan. 16, 2013 for U.S. Appl. No. 13/493,898.
Office Communication dated Jan. 28, 2013 for U.S. Appl. No. 12/809,181.
Office Communication dated Feb. 15, 2013 for U.S. Appl. No. 12/921,036.
Office Communication dated Feb. 25, 2013 for U.S. Appl. No. 12/866,594.
Office Communication dated Apr. 4, 2013 for U.S. Appl. No. 12/746,674.
Office Communication dated Apr. 12, 2013 for U.S. Appl. No. 12/450,358.
Office Communication dated Jun. 19, 2013 for U.S. Appl. No. 13/379,872.
Office Communication dated Jul. 10, 2013 for U.S. Appl. No. 12/809,181.
Office Communication dated Jul. 12, 2013 for U.S. Appl. No. 13/493,898.
Office Communication dated Jul. 22, 2013 for U.S. Appl. No. 12/866,594.
Office Communication dated Sep. 27, 2013 for U.S. Appl. No. 12/450,358.
Office Communication dated Oct. 31, 2013 for U.S. Appl. No. 13/817,858.
Office Communication dated Jan. 3, 2014 for U.S. Appl. No. 12/866,594.
Office Communication dated Jan. 27, 2014 for U.S. Appl. No. 12/450,358.
Office Communication dated Feb. 7, 2014 for U.S. Appl. No. 13/493,898.
Office Communication dated Mar. 11, 2014 for U.S. Appl. No. 13/817,858.
Office Communication dated Jul. 28, 2014 for U.S. Appl. No. 12/866,594.

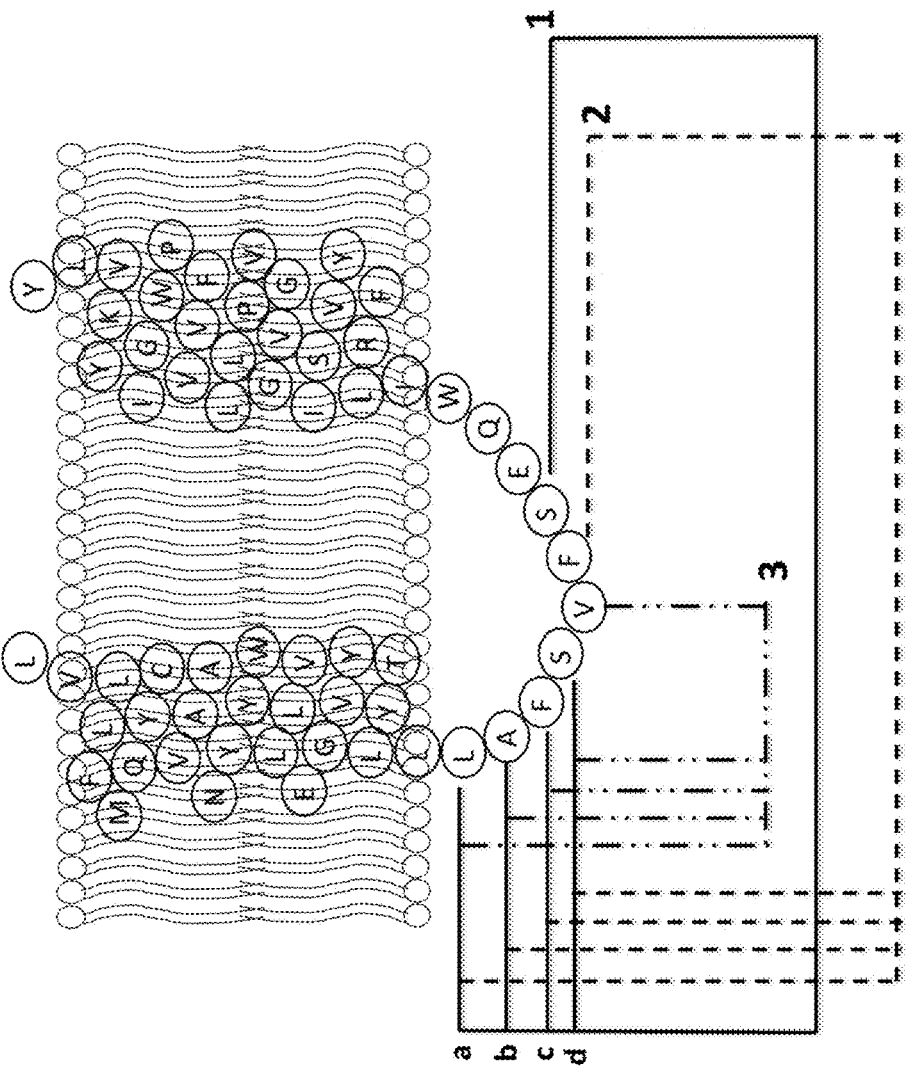

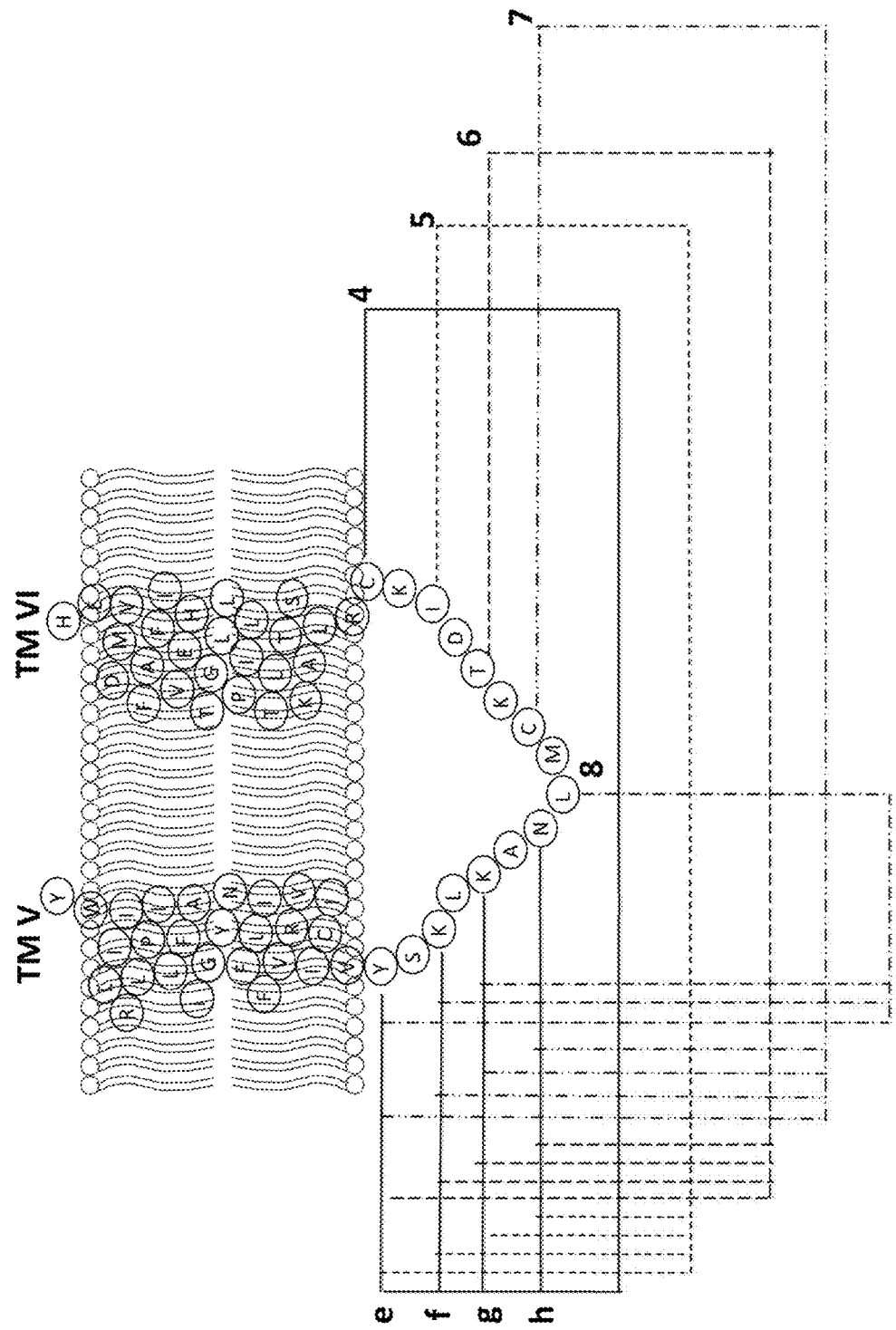

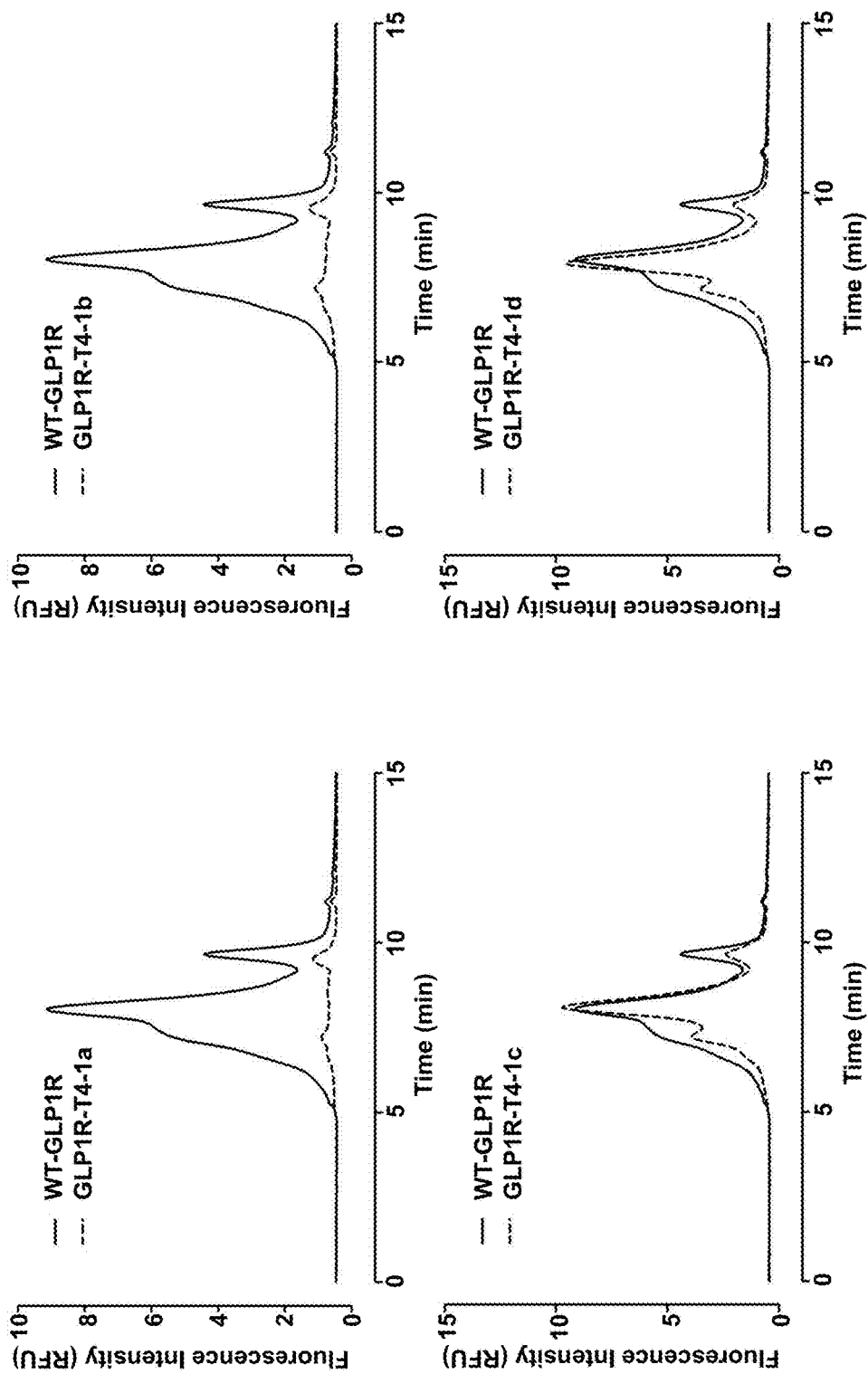

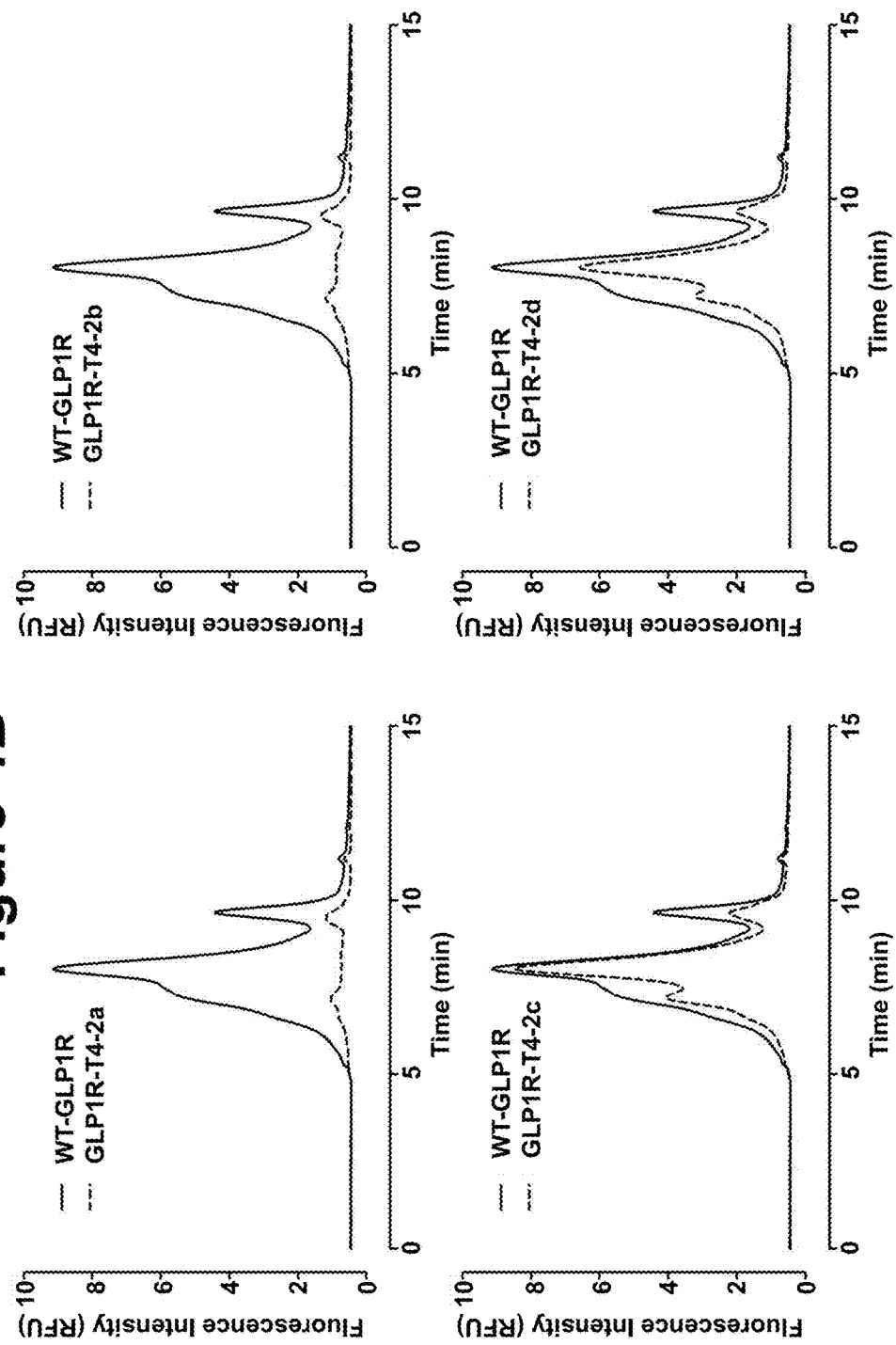

Figure 6

```
                    ---->┌─┐<---------- HLX4 ------>              <-------
PTHR1_RAT      SLIFM│AFF│SEKKYLWGFTIFGWGLPAVFVAVWVGVRATLANTGCWDLSSG--HKKWIIQV
PTHR1_MOUSE    SLIFM│AFF│SEKKYLWGFTIFGWGLPAVFVAVWVGVRATLANTGCWDLSSG--HKKWIIQV
PTHR1_HUMAN    SLIFM│AFF│SEKKYLWGFTVFGWGLPAVFVAVWVSVRATLANTGCWDLSSG--NKKWIIQV
PTHR2_MOUSE    NLIFV│SFF│SDTKYLWGFISIGWGFPAVFVVAWAVARATLADTRCWELSA---GDRWIYQA
PTHR2_RAT      NLIFV│SFF│SDTKYLWGFILIGWGFPAVFVVAWAVARATLADTRCWE---LSAGDRWIYXX
PTHR2_HUMAN    NLIFV│AFF│SDTKYLWGFILIGWGFPAAFVAAWAVARATLADARCWEL--SAGDIKWIYQA
GHRHR_MOUSE    CLLAS│TSF│RSKPAFWWLVLAGWGLPVLCTGTWVGCKHSFEDTECWDLDNS-SPCWWIIKG
GHRHR_RAT      CLLAS│TSF│RSKPAFWWLVLAGWGLPVLCTGTWVGCKLAFEDTACWDLDDS-SPYWWIIKG
GHRHR_HUMAN    CLLAS│TSF│SSRRAFWWLVLAGWGLPVLFTGTWVSCKLAFEDIACWDLDDT-SPYWWIIKG
PACR_MOUSE     TLLVE│TFF│PERRYFYWYTIIGWGTPTVCVTVWAVLRLYFDDAGCWDMNDS-TALWWVIKG
PACR_RAT       TLLVE│TFF│PERRYFYWYTIIGWGTPTVCVTVWAVLRLYFDDAGCWDMNDS-TALWWVIKG
PACR_HUMAN     TLLVE│TFF│PERRYFYWYTIIGWGTPTVCVTVWATLRLYFDDTGCWDMNDS-TALWWVIKG
VIPR2_MOUSE    TLLVA│IL-│PPSRCFLAYLLIGWGIPSVCIGAWTATRLSLEDTGCWDTNDH-SIPWWVIRM
VIPR2_RAT      TLLVA│IL-│PPSRCFLAYLLIGWGIPSVCIGAWIATRLSLEDTGCWDTNDH-SIPWWVIRM
VIPR2_HUMAN    TLLVA│ML-│PPRRCFLAYLLIGWGLPTVCIGAWTAARLYLEDTGCWDTNDH-SVPWWVIRI
VIPR1_MOUSE    TLLAV│SFF│SERKYFWGYILIGWGVPSVFIMIWTIVRIHFEDFGCWDTIIN-SSLWWIIKG
VIPR1_RAT      TLLAV│SFF│SERKYFWGYILIGWGVPSVFITIWTVVRIYFEDFGCWDTIIN-SSLWWIIKA
VIPR1_HUMAN    TLLAV│SFF│SERKYFWGYILIGWGVPSTFTMVWTIARIHFEDYGCWDT-IN-SSLWWIIKG
SCTR_HUMAN     TLLAI│SFF│SERKYLQGFVAFGWGSPAIFVALWAIARHFLEDVGCWDINAN-ASIWWIIRG
SCTR_RAT       TLLAI│SFF│SERKYLQAFVLLGWGSPAIFVALWAITRHFLENTGCWDINAN-ASVWWVIRG
GLR_MOUSE      SLLSL│ATF│SERSFFSLYLGIGWGAPLLFVIPWVVVKCLFENVQCWTSNDN-MGFWWILRI
GLR_RAT        SLLSI│PTF│SEKSFFSLYLCIGWGSPLLFVIPWVVVKCLFENVQCWTSNDN-MGFWWILRI
GLR_HUMAN      NLLGL│ATI│PERSFFSLYLGIGWGAPMLFVVPWAVVKCLFENVQCWTSNDN-MGFWWILRF
GIPR_HUMAN     SLLVL│VGG│SEEGHFRYYLLLGWGAPALFVIPWVIVRYLYENTQCWERNEV-KAIWWIIRT
GIPR_RAT       HLLVV│VRR│SEKGHFRCYLLLGWGAPALFVIPWVIVRYLYENTQCWERNEV-KAIWWIIRT
GLP1R_MOUSE    TLLAF│SVF│SEQRIFKLYLSIGWGVPLLFVIPWGIVKYLYEDEGCWTRNSN-MNYWLIIRL
GLP1R_RAT      TLLAF│SVF│SEQRIFKLYLSIGWGVPLLFVIPWGIVKYLYEDEGCWTRNSN-MNYWLIIRL
GLP1R_HUMAN    TLLAF│SVF│SEQWIFRLYVSIGWGVPLLFVVPWGIVKYLYEDEGCWTRNSN-MNYWLIIRL
GLP2R_HUMAN    TLLEP│TVL│PERRLWPRYLLLGWAFPMLFVVPWGFARAHLENTGCWTTNGN-KKIWWIIRG
GLP2R_RAT      TLLEP│TVF│PERRLWPKYLVVGWAFPMLFVVPWGFARAHLENTRCWATNGN-LKIWWIIRG
CRFR1_HUMAN    TAIVL│TYS│TDRLRKWMFICIGWGVPFPIIVAWAIGKLYYDNEKCWFGKRPGVYTDYIYQG
CRFR1_MOUSE    TAIVL│TYS│TDRLRKWMFVCIGWGVPFPIIVAWAIGKLYYDNEKCWFGKRPGVYTDYIYQG
CRFR1_RAT      TAIVL│TYS│TDRLRKWMFVCIGWGVPFPIIVAWAIGKLHYDNEKCWFGKRPGVYTDYIYQG
CRFR2_HUMAN    TAIVM│TYS│TERLRKCLFLFIGWCIPFPIIVAWAIGKLYYENEQCWFGKEPGDLVDYIYQG
CRFR2_RAT      TAIVM│TYS│TEHLRKWLFLFIGWCIPCPIIVAWAVGKLYYENEQCWFGKEPGDLVDYIYQG
CRFR2_MOUSE    TAIVM│TYS│TEHLRKWLFLFIGWCIPCPIIIAWAVGKLYYENEQCWFGKEAGDLVDYIYQG
CALCR_MOUSE    TLIVM│AVF│TDEQRLRWYYLLGWGFPIVPTIIHAITRALYYNDNCWLSAET--HLLYIIHG
CALCR_RAT      TLIVM│AVF│TEDQRLRWYYLLGWGFPIVPTIIHAITRAVYFNDNCWLSTET--HLLYIIHG
CALCR_HUMAN    TLIVV│AVF│TEKQRLRWYYLLGWGFPLVPTTIHAITRAVYFNDNCWLSVET--HLLYIIHG
CALRL_MOUSE    TLIVV│AVF│AEKQHLMWYYFLGWGFPLLPACIHAIARSLYYNDNCWISSDT--HLLYIIHG
CALRL_RAT      TLIVV│AVF│AEKQHLMWYYFLGWGFPLLPACIHAIARSLYYNDNCWISSDT--HLLYIIHG
CALRL_HUMAN    TLIVV│AVF│AEKQHLMWYYFLGWGFPLIPACIHAIARSLYYNDNCWISSDT--HLLYIIHG
                    └─┘:            ** *             :   : **            :
```

Figure 7

A.

MNIFEMLRIDEGLRLRLKIYKDTEGYYTIGIGHLLLTKSPSL[NA]AKSELDKAIGRN[T]NGVITKDEAEKLFNQD
VDAAVRGILRNAKLKPVYDSLDAVRR[A]ALINMVFQMGETGVAGFTNSLRMLQQKRWDEAAVNLAKSRWYN
QTPNRAKRVI[T]TFRTGTWDAYKNL

B.

MNIFEMLRIDEGLRLRLKIYKDTEGYYTIGIGHLLLTKSPSL[SV]AKSELDKAIGRN[S]NGVITKDEAEKLFNQD
VDAAVRGILRNAKLKPVYDSLDAVRR[S]ALINMVFQMGETGVAGFTNSLRMLQQKRWDEAAVNLAKSRWYN
QTPNRAKRVI[A]TFRTGTWDAYKNL

SEQUENCE LISTING

<160> NUMBER OF SEQ ID NOS: 44

<210> SEQ ID NO 1
<211> LENGTH: 58
<212> TYPE: PRT
<213> ORGANISM: Rattus rattus

<400> SEQUENCE: 1

Ser Leu Ile Phe Met Ala Phe Phe Ser Glu Lys Lys Tyr Leu Trp Gly
1               5                   10                  15

Phe Thr Ile Phe Gly Trp Gly Leu Pro Ala Val Phe Val Ala Val Trp
            20                  25                  30

Val Gly Val Arg Ala Thr Leu Ala Asn Thr Gly Cys Trp Asp Leu Ser
        35                  40                  45

Ser Gly His Lys Lys Trp Ile Ile Gln Val
    50                  55

<210> SEQ ID NO 2
<211> LENGTH: 58
<212> TYPE: PRT
<213> ORGANISM: Mus musculus

<400> SEQUENCE: 2

Ser Leu Ile Phe Met Ala Phe Phe Ser Glu Lys Lys Tyr Leu Trp Gly
1               5                   10                  15

Phe Thr Ile Phe Gly Trp Gly Leu Pro Ala Val Phe Val Ala Val Trp
            20                  25                  30

Val Gly Val Arg Ala Thr Leu Ala Asn Thr Gly Cys Trp Asp Leu Ser
        35                  40                  45

Ser Gly His Lys Lys Trp Ile Ile Gln Val
    50                  55

<210> SEQ ID NO 3
<211> LENGTH: 58
<212> TYPE: PRT
<213> ORGANISM: Homo sapiens

<400> SEQUENCE: 3

Ser Leu Ile Phe Met Ala Phe Phe Ser Glu Lys Lys Tyr Leu Trp Gly
1               5                   10                  15

Phe Thr Val Phe Gly Trp Gly Leu Pro Ala Val Phe Val Ala Val Trp
            20                  25                  30

Val Ser Val Arg Ala Thr Leu Ala Asn Thr Gly Cys Trp Asp Leu Ser
        35                  40                  45

Ser Gly Asn Lys Lys Trp Ile Ile Gln Val
    50                  55

<210> SEQ ID NO 4
<211> LENGTH: 57
<212> TYPE: PRT
<213> ORGANISM: Mus musculus

<400> SEQUENCE: 4

Asn Leu Ile Phe Val Ser Phe Phe Ser Asp Thr Lys Tyr Leu Trp Gly
1               5                   10                  15

Phe Ile Ser Ile Gly Trp Gly Phe Pro Ala Val Phe Val Ala Trp
            20                  25                  30

Ala Val Ala Arg Ala Thr Leu Ala Asp Thr Arg Cys Trp Glu Leu Ser
            35                  40                  45

Ala Gly Asp Arg Trp Ile Tyr Gln Ala
    50                  55

<210> SEQ ID NO 5
<211> LENGTH: 57
<212> TYPE: PRT
<213> ORGANISM: Rattus rattus
<220> FEATURE:
<221> NAME/KEY: UNSURE
<222> LOCATION: (56)..(57)
<223> OTHER INFORMATION: UNSURE

<400> SEQUENCE: 5

Asn Leu Ile Phe Val Ser Phe Phe Ser Asp Thr Lys Tyr Leu Trp Gly
1               5                   10                  15

Phe Ile Leu Ile Gly Trp Gly Phe Pro Ala Val Phe Val Val Ala Trp
            20                  25                  30

Ala Val Ala Arg Ala Thr Leu Ala Asp Thr Arg Cys Trp Glu Leu Ser
            35                  40                  45

Ala Gly Asp Arg Trp Ile Tyr Xaa Xaa
    50                  55

<210> SEQ ID NO 6
<211> LENGTH: 58
<212> TYPE: PRT
<213> ORGANISM: Homo sapiens

<400> SEQUENCE: 6

Asn Leu Ile Phe Val Ala Phe Phe Ser Asp Thr Lys Tyr Leu Trp Gly
1               5                   10                  15

Phe Ile Leu Ile Gly Trp Gly Phe Pro Ala Ala Phe Val Ala Ala Trp
            20                  25                  30

Ala Val Ala Arg Ala Thr Leu Ala Asp Ala Arg Cys Trp Glu Leu Ser
            35                  40                  45

Ala Gly Asp Ile Lys Trp Ile Tyr Gln Ala
    50                  55

<210> SEQ ID NO 7
<211> LENGTH: 59
<212> TYPE: PRT
<213> ORGANISM: Mus musculus

<400> SEQUENCE: 7

Cys Leu Leu Ala Ser Thr Ser Pro Arg Ser Lys Pro Ala Phe Trp Trp
1               5                   10                  15

Leu Val Leu Ala Gly Trp Gly Leu Pro Val Leu Cys Thr Gly Thr Trp
            20                  25                  30

Val Gly Cys Lys His Ser Phe Glu Asp Thr Glu Cys Trp Asp Leu Asp
            35                  40                  45

Asn Ser Ser Pro Cys Trp Trp Ile Ile Lys Gly
    50                  55

<210> SEQ ID NO 8
<211> LENGTH: 59
<212> TYPE: PRT
<213> ORGANISM: Rattus rattus

```
<400> SEQUENCE: 8

Cys Leu Leu Ala Ser Thr Ser Pro Arg Ser Lys Pro Ala Phe Trp Trp
1               5                   10                  15

Leu Val Leu Ala Gly Trp Gly Leu Pro Val Leu Cys Thr Gly Thr Trp
                20                  25                  30

Val Gly Cys Lys Leu Ala Phe Glu Asp Thr Ala Cys Trp Asp Leu Asp
            35                  40                  45

Asp Ser Ser Pro Tyr Trp Trp Ile Ile Lys Gly
    50                  55

<210> SEQ ID NO 9
<211> LENGTH: 59
<212> TYPE: PRT
<213> ORGANISM: Homo sapiens

<400> SEQUENCE: 9

Cys Leu Leu Ala Ser Thr Ser Pro Ser Ser Arg Ala Phe Trp Trp
1               5                   10                  15

Leu Val Leu Ala Gly Trp Gly Leu Pro Val Leu Phe Thr Gly Thr Trp
                20                  25                  30

Val Ser Cys Lys Leu Ala Phe Glu Asp Ile Ala Cys Trp Asp Leu Asp
            35                  40                  45

Asp Thr Ser Pro Tyr Trp Trp Ile Ile Lys Gly
    50                  55

<210> SEQ ID NO 10
<211> LENGTH: 59
<212> TYPE: PRT
<213> ORGANISM: Mus musculus

<400> SEQUENCE: 10

Thr Leu Leu Val Glu Thr Phe Phe Pro Glu Arg Arg Tyr Phe Tyr Trp
1               5                   10                  15

Tyr Thr Ile Ile Gly Trp Gly Thr Pro Thr Val Cys Val Thr Val Trp
                20                  25                  30

Ala Val Leu Arg Leu Tyr Phe Asp Asp Ala Gly Cys Trp Asp Met Asn
            35                  40                  45

Asp Ser Thr Ala Leu Trp Trp Val Ile Lys Gly
    50                  55

<210> SEQ ID NO 11
<211> LENGTH: 59
<212> TYPE: PRT
<213> ORGANISM: Rattus rattus

<400> SEQUENCE: 11

Thr Leu Leu Val Glu Thr Phe Phe Pro Glu Arg Arg Tyr Phe Tyr Trp
1               5                   10                  15

Tyr Thr Ile Ile Gly Trp Gly Thr Pro Thr Val Cys Val Thr Val Trp
                20                  25                  30

Ala Val Leu Arg Leu Tyr Phe Asp Asp Ala Gly Cys Trp Asp Met Asn
            35                  40                  45

Asp Ser Thr Ala Leu Trp Trp Val Ile Lys Gly
    50                  55

<210> SEQ ID NO 12
<211> LENGTH: 58
<212> TYPE: PRT
<213> ORGANISM: Homo sapiens
```

<400> SEQUENCE: 12

Thr Leu Leu Val Glu Thr Phe Phe Pro Glu Arg Arg Tyr Phe Tyr Trp
1               5                   10                  15

Thr Ile Ile Gly Trp Gly Thr Pro Val Cys Val Thr Val Trp Ala
            20                  25                  30

Thr Leu Arg Leu Tyr Phe Asp Asp Thr Gly Cys Trp Asp Met Asn Asp
        35                  40                  45

Ser Thr Ala Leu Trp Trp Val Ile Lys Gly
    50                  55

<210> SEQ ID NO 13
<211> LENGTH: 58
<212> TYPE: PRT
<213> ORGANISM: Mus musculus

<400> SEQUENCE: 13

Thr Leu Leu Val Ala Ile Leu Pro Pro Ser Arg Cys Phe Leu Ala Tyr
1               5                   10                  15

Leu Leu Ile Gly Trp Gly Ile Pro Ser Val Cys Ile Gly Ala Trp Thr
            20                  25                  30

Ala Thr Arg Leu Ser Leu Glu Asp Thr Gly Cys Trp Asp Thr Asn Asp
        35                  40                  45

His Ser Ile Pro Trp Trp Val Ile Arg Met
    50                  55

<210> SEQ ID NO 14
<211> LENGTH: 58
<212> TYPE: PRT
<213> ORGANISM: Rattus rattus

<400> SEQUENCE: 14

Thr Leu Leu Val Ala Ile Leu Pro Pro Ser Arg Cys Phe Leu Ala Tyr
1               5                   10                  15

Leu Leu Ile Gly Trp Gly Ile Pro Ser Val Cys Ile Gly Ala Trp Ile
            20                  25                  30

Ala Thr Arg Leu Ser Leu Glu Asp Thr Gly Cys Trp Asp Thr Asn Asp
        35                  40                  45

His Ser Ile Pro Trp Trp Val Ile Arg Met
    50                  55

<210> SEQ ID NO 15
<211> LENGTH: 58
<212> TYPE: PRT
<213> ORGANISM: Homo sapiens

<400> SEQUENCE: 15

Thr Leu Leu Val Ala Met Leu Pro Pro Arg Arg Cys Phe Leu Ala Tyr
1               5                   10                  15

Leu Leu Ile Gly Trp Gly Leu Pro Thr Val Cys Ile Gly Ala Trp Thr
            20                  25                  30

Ala Ala Arg Leu Tyr Leu Glu Asp Thr Gly Cys Trp Asp Thr Asn Asp
        35                  40                  45

His Ser Val Pro Trp Trp Val Ile Arg Ile
    50                  55

<210> SEQ ID NO 16
<211> LENGTH: 59
<212> TYPE: PRT
<213> ORGANISM: Mus musculus

```
<400> SEQUENCE: 16

Thr Leu Leu Ala Val Ser Phe Phe Ser Glu Arg Lys Tyr Phe Trp Gly
1               5                   10                  15

Tyr Ile Leu Ile Gly Trp Gly Val Pro Ser Val Phe Ile Met Ile Trp
                20                  25                  30

Thr Ile Val Arg Ile His Phe Glu Asp Phe Gly Cys Trp Asp Thr Ile
                35                  40                  45

Ile Asn Ser Ser Leu Trp Trp Ile Ile Lys Gly
                50                  55

<210> SEQ ID NO 17
<211> LENGTH: 59
<212> TYPE: PRT
<213> ORGANISM: Rattus rattus

<400> SEQUENCE: 17

Thr Leu Leu Ala Val Ser Phe Phe Ser Glu Arg Lys Tyr Phe Trp Gly
1               5                   10                  15

Tyr Ile Leu Ile Gly Trp Gly Val Pro Ser Val Phe Ile Thr Ile Trp
                20                  25                  30

Thr Val Val Arg Ile Tyr Phe Glu Asp Phe Gly Cys Trp Asp Thr Ile
                35                  40                  45

Ile Asn Ser Ser Leu Trp Trp Ile Ile Lys Ala
                50                  55

<210> SEQ ID NO 18
<211> LENGTH: 58
<212> TYPE: PRT
<213> ORGANISM: Homo sapiens

<400> SEQUENCE: 18

Thr Leu Leu Ala Val Ser Phe Phe Ser Glu Arg Lys Tyr Phe Trp Gly
1               5                   10                  15

Tyr Ile Leu Ile Gly Trp Gly Val Pro Ser Thr Phe Thr Met Val Trp
                20                  25                  30

Thr Ile Ala Arg Ile His Phe Glu Asp Tyr Gly Cys Trp Asp Thr Ile
                35                  40                  45

Asn Ser Ser Leu Trp Trp Ile Ile Lys Gly
            50                  55

<210> SEQ ID NO 19
<211> LENGTH: 59
<212> TYPE: PRT
<213> ORGANISM: Homo sapiens

<400> SEQUENCE: 19

Thr Leu Leu Ala Ile Ser Phe Phe Ser Glu Arg Lys Tyr Leu Gln Gly
1               5                   10                  15

Phe Val Ala Phe Gly Trp Gly Ser Pro Ala Ile Phe Val Ala Leu Trp
                20                  25                  30

Ala Ile Ala Arg His Phe Leu Glu Asp Val Gly Cys Trp Asp Ile Asn
                35                  40                  45

Ala Asn Ala Ser Ile Trp Trp Ile Ile Arg Gly
                50                  55

<210> SEQ ID NO 20
<211> LENGTH: 59
<212> TYPE: PRT
<213> ORGANISM: Rattus rattus
```

```
<400> SEQUENCE: 20

Thr Leu Leu Ala Ile Ser Phe Ser Glu Arg Lys Tyr Leu Gln Ala
1               5                   10                  15

Phe Val Leu Leu Gly Trp Gly Ser Pro Ala Ile Phe Val Ala Leu Trp
            20                  25                  30

Ala Ile Thr Arg His Phe Leu Glu Asn Thr Gly Cys Trp Asp Ile Asn
        35                  40                  45

Ala Asn Ala Ser Val Trp Trp Val Ile Arg Gly
    50                  55

<210> SEQ ID NO 21
<211> LENGTH: 59
<212> TYPE: PRT
<213> ORGANISM: Mus musculus

<400> SEQUENCE: 21

Ser Leu Leu Ser Leu Ala Thr Phe Ser Glu Arg Ser Phe Phe Ser Leu
1               5                   10                  15

Tyr Leu Gly Ile Gly Trp Gly Ala Pro Leu Leu Phe Val Ile Pro Trp
            20                  25                  30

Val Val Val Lys Cys Leu Phe Glu Asn Val Gln Cys Trp Thr Ser Asn
        35                  40                  45

Asp Asn Met Gly Phe Trp Trp Ile Leu Arg Ile
    50                  55

<210> SEQ ID NO 22
<211> LENGTH: 59
<212> TYPE: PRT
<213> ORGANISM: Rattus rattus

<400> SEQUENCE: 22

Ser Leu Leu Ser Ile Thr Thr Phe Ser Glu Lys Ser Phe Phe Ser Leu
1               5                   10                  15

Tyr Leu Cys Ile Gly Trp Gly Ser Pro Leu Leu Phe Val Ile Pro Trp
            20                  25                  30

Val Val Val Lys Cys Leu Phe Glu Asn Val Gln Cys Trp Thr Ser Asn
        35                  40                  45

Asp Asn Met Gly Phe Trp Trp Ile Leu Arg Ile
    50                  55

<210> SEQ ID NO 23
<211> LENGTH: 164
<212> TYPE: PRT
<213> ORGANISM: T4 phage

<400> SEQUENCE: 23

Met Asn Ile Phe Glu Met Leu Arg Ile Asp Glu Gly Leu Arg Leu Lys
1               5                   10                  15

Ile Tyr Lys Asp Thr Glu Gly Tyr Tyr Thr Ile Gly Ile Gly His Leu
            20                  25                  30

Leu Thr Lys Ser Pro Ser Leu Asn Ala Ala Lys Ser Glu Leu Asp Lys
        35                  40                  45

Ala Ile Gly Arg Asn Thr Asn Gly Val Ile Thr Lys Asp Glu Ala Glu
    50                  55                  60

Lys Leu Phe Asn Gln Asp Val Asp Ala Ala Val Arg Gly Ile Leu Arg
65                  70                  75                  80

Asn Ala Lys Leu Lys Pro Val Tyr Asp Ser Leu Asp Ala Val Arg Arg
                85                  90                  95
```

Ala Ala Leu Ile Asn Met Val Phe Gln Met Gly Glu Thr Gly Val Ala
            100                 105                 110

Gly Phe Thr Asn Ser Leu Arg Met Leu Gln Gln Lys Arg Trp Asp Glu
        115                 120                 125

Ala Ala Val Asn Leu Ala Lys Ser Arg Trp Tyr Asn Gln Thr Pro Asn
130                 135                 140

Arg Ala Lys Arg Val Ile Thr Thr Phe Arg Thr Gly Thr Trp Asp Ala
145                 150                 155                 160

Tyr Lys Asn Leu

<210> SEQ ID NO 24
<211> LENGTH: 164
<212> TYPE: PRT
<213> ORGANISM: T4 phage

<400> SEQUENCE: 24

Met Asn Ile Phe Glu Met Leu Arg Ile Asp Glu Gly Leu Arg Leu Lys
1               5                   10                  15

Ile Tyr Lys Asp Thr Glu Gly Tyr Tyr Thr Ile Gly Ile Gly His Leu
            20                  25                  30

Leu Thr Lys Ser Pro Ser Leu Ser Val Ala Lys Ser Glu Leu Asp Lys
        35                  40                  45

Ala Ile Gly Arg Asn Ser Asn Gly Val Ile Thr Lys Asp Glu Ala Glu
    50                  55                  60

Lys Leu Phe Asn Gln Asp Val Asp Ala Ala Val Arg Gly Ile Leu Arg
65                  70                  75                  80

Asn Ala Lys Leu Lys Pro Val Tyr Asp Ser Leu Asp Ala Val Arg Arg
                85                  90                  95

Ser Ala Leu Ile Asn Met Val Phe Gln Met Gly Glu Thr Gly Val Ala
            100                 105                 110

Gly Phe Thr Asn Ser Leu Arg Met Leu Gln Gln Lys Arg Trp Asp Glu
        115                 120                 125

Ala Ala Val Asn Leu Ala Lys Ser Arg Trp Tyr Asn Gln Thr Pro Asn
130                 135                 140

Arg Ala Lys Arg Val Ile Ala Thr Phe Arg Thr Gly Thr Trp Asp Ala
145                 150                 155                 160

Tyr Lys Asn Leu

<210> SEQ ID NO 25
<211> LENGTH: 59
<212> TYPE: PRT
<213> ORGANISM: Homo sapiens

<400> SEQUENCE: 25

Asn Leu Leu Gly Leu Ala Thr Leu Pro Glu Arg Ser Phe Phe Ser Leu
1               5                   10                  15

Tyr Leu Gly Ile Gly Trp Gly Ala Pro Met Leu Phe Val Pro Trp
            20                  25                  30

Ala Val Val Lys Cys Leu Phe Glu Asn Val Gln Cys Trp Thr Ser Asn
            35                  40                  45

Asp Asn Met Gly Phe Trp Trp Ile Leu Arg Phe
        50                  55

<210> SEQ ID NO 26
<211> LENGTH: 59
<212> TYPE: PRT
<213> ORGANISM: Homo sapiens -continued

```
<400> SEQUENCE: 26

Ser Leu Leu Val Leu Val Gly Gly Ser Glu Glu Gly His Phe Arg Tyr
1               5                   10                  15

Tyr Leu Leu Gly Trp Gly Ala Pro Ala Leu Phe Val Ile Pro Trp
            20                  25                  30

Val Ile Val Arg Tyr Leu Tyr Glu Asn Thr Gln Cys Trp Glu Arg Asn
        35                  40                  45

Glu Val Lys Ala Ile Trp Trp Ile Ile Arg Thr
    50                  55

<210> SEQ ID NO 27
<211> LENGTH: 59
<212> TYPE: PRT
<213> ORGANISM: Rattus rattus

<400> SEQUENCE: 27

His Leu Leu Val Val Arg Arg Ser Glu Lys Gly His Phe Arg Cys
1               5                   10                  15

Tyr Leu Leu Gly Trp Gly Ala Pro Ala Leu Phe Val Ile Pro Trp
            20                  25                  30

Val Ile Val Arg Tyr Leu Tyr Glu Asn Thr Gln Cys Trp Glu Arg Asn
        35                  40                  45

Glu Val Lys Ala Ile Trp Trp Ile Ile Arg Thr
    50                  55

<210> SEQ ID NO 28
<211> LENGTH: 59
<212> TYPE: PRT
<213> ORGANISM: Mus musculus

<400> SEQUENCE: 28

Thr Thr Leu Ala Phe Ser Val Phe Ser Glu Gln Arg Ile Phe Lys Leu
1               5                   10                  15

Tyr Leu Ser Ile Gly Trp Gly Val Pro Leu Leu Phe Val Ile Pro Trp
            20                  25                  30

Gly Ile Val Lys Tyr Leu Tyr Glu Asp Glu Gly Cys Trp Thr Arg Asn
        35                  40                  45

Ser Asn Met Asn Tyr Trp Leu Ile Ile Arg Leu
    50                  55

<210> SEQ ID NO 29
<211> LENGTH: 59
<212> TYPE: PRT
<213> ORGANISM: Rattus rattus

<400> SEQUENCE: 29

Thr Leu Leu Ala Phe Ser Val Phe Ser Glu Gln Arg Ile Phe Lys Leu
1               5                   10                  15

Tyr Leu Ser Ile Gly Trp Gly Val Pro Leu Leu Phe Val Ile Pro Trp
            20                  25                  30

Gly Ile Val Lys Tyr Leu Tyr Glu Asp Glu Gly Cys Trp Thr Arg Asn
        35                  40                  45

Ser Asn Met Asn Tyr Trp Leu Ile Ile Arg Leu
    50                  55

<210> SEQ ID NO 30
<211> LENGTH: 59
<212> TYPE: PRT
<213> ORGANISM: Homo sapiens
```

<400> SEQUENCE: 30

Thr Leu Leu Ala Phe Ser Val Phe Ser Glu Gln Trp Ile Phe Arg Leu
1               5                   10                  15

Tyr Val Ser Ile Gly Trp Gly Val Pro Leu Leu Phe Val Val Pro Trp
            20                  25                  30

Gly Ile Val Lys Tyr Leu Tyr Glu Asp Glu Gly Cys Trp Thr Arg Asn
        35                  40                  45

Ser Asn Met Asn Tyr Trp Leu Ile Ile Arg Leu
    50                  55

<210> SEQ ID NO 31
<211> LENGTH: 59
<212> TYPE: PRT
<213> ORGANISM: Homo sapiens

<400> SEQUENCE: 31

Thr Leu Leu Glu Pro Thr Val Leu Pro Glu Arg Arg Leu Trp Pro Arg
1               5                   10                  15

Tyr Leu Leu Gly Trp Ala Phe Pro Val Leu Phe Val Val Pro Trp
            20                  25                  30

Gly Phe Ala Arg Ala His Leu Glu Asn Thr Gly Cys Trp Thr Thr Asn
        35                  40                  45

Gly Asn Lys Lys Ile Trp Trp Ile Ile Arg Gly
    50                  55

<210> SEQ ID NO 32
<211> LENGTH: 59
<212> TYPE: PRT
<213> ORGANISM: Rattus rattus

<400> SEQUENCE: 32

Thr Leu Leu Glu Pro Thr Val Phe Pro Glu Arg Arg Leu Trp Pro Lys
1               5                   10                  15

Tyr Leu Val Val Gly Trp Ala Phe Pro Met Leu Phe Val Ile Pro Trp
            20                  25                  30

Gly Phe Ala Arg Ala His Leu Glu Asn Thr Arg Cys Trp Ala Thr Asn
        35                  40                  45

Gly Asn Leu Lys Ile Trp Trp Ile Ile Arg Gly
    50                  55

<210> SEQ ID NO 33
<211> LENGTH: 60
<212> TYPE: PRT
<213> ORGANISM: Homo sapiens

<400> SEQUENCE: 33

Thr Ala Ile Val Leu Thr Tyr Ser Thr Asp Arg Leu Arg Lys Trp Met
1               5                   10                  15

Phe Ile Cys Ile Gly Trp Gly Val Pro Phe Pro Ile Ile Val Ala Trp
            20                  25                  30

Ala Ile Gly Lys Leu Tyr Tyr Asp Asn Glu Lys Cys Trp Phe Gly Lys
        35                  40                  45

Arg Pro Gly Val Tyr Thr Asp Tyr Ile Tyr Gln Gly
    50                  55                  60

<210> SEQ ID NO 34
<211> LENGTH: 60
<212> TYPE: PRT
<213> ORGANISM: Mus musculus

```
<400> SEQUENCE: 34

Thr Ala Ile Val Leu Thr Tyr Ser Thr Asp Arg Leu Arg Lys Trp Met
1               5                   10                  15

Phe Val Cys Ile Gly Trp Gly Val Pro Phe Pro Ile Ile Val Ala Trp
                20                  25                  30

Ala Ile Gly Lys Leu Tyr Tyr Asp Asn Glu Lys Cys Trp Phe Gly Lys
                35                  40                  45

Arg Pro Gly Val Tyr Thr Asp Tyr Ile Tyr Gln Gly
            50                  55                  60

<210> SEQ ID NO 35
<211> LENGTH: 60
<212> TYPE: PRT
<213> ORGANISM: Rattus rattus

<400> SEQUENCE: 35

Thr Ala Ile Val Leu Thr Tyr Ser Thr Asp Arg Leu Arg Lys Trp Met
1               5                   10                  15

Phe Val Cys Ile Gly Trp Gly Val Pro Phe Pro Ile Ile Val Ala Trp
                20                  25                  30

Ala Ile Gly Lys Leu His Tyr Asp Asn Glu Lys Cys Trp Phe Gly Lys
                35                  40                  45

Arg Pro Gly Val Tyr Thr Asp Tyr Ile Tyr Gln Gly
            50                  55                  60

<210> SEQ ID NO 36
<211> LENGTH: 60
<212> TYPE: PRT
<213> ORGANISM: Homo sapiens

<400> SEQUENCE: 36

Thr Ala Ile Val Met Thr Tyr Ser Thr Glu Arg Leu Arg Lys Cys Leu
1               5                   10                  15

Phe Leu Phe Ile Gly Trp Cys Ile Pro Phe Pro Ile Ile Val Ala Trp
                20                  25                  30

Ala Ile Gly Lys Leu Tyr Tyr Glu Asn Glu Gln Cys Trp Phe Gly Lys
                35                  40                  45

Glu Pro Gly Asp Leu Val Asp Tyr Ile Tyr Gln Gly
            50                  55                  60

<210> SEQ ID NO 37
<211> LENGTH: 60
<212> TYPE: PRT
<213> ORGANISM: Rattus rattus

<400> SEQUENCE: 37

Thr Ala Ile Val Met Thr Tyr Ser Thr Glu His Leu Arg Lys Trp Leu
1               5                   10                  15

Phe Leu Phe Ile Gly Trp Cys Ile Pro Cys Pro Ile Ile Val Ala Trp
                20                  25                  30

Ala Val Gly Lys Leu Tyr Tyr Glu Asn Glu Gln Cys Trp Phe Gly Lys
                35                  40                  45

Glu Pro Gly Asp Leu Val Asp Tyr Ile Tyr Gln Gly
            50                  55                  60

<210> SEQ ID NO 38
<211> LENGTH: 60
<212> TYPE: PRT
<213> ORGANISM: Mus musculus
```

-continued

<400> SEQUENCE: 38

Thr Ala Ile Val Met Thr Tyr Ser Thr Glu His Leu Arg Lys Trp Leu
1               5                   10                  15

Phe Leu Phe Ile Gly Trp Cys Ile Pro Cys Pro Ile Ile Ala Trp
            20                  25                  30

Ala Val Gly Lys Leu Tyr Tyr Glu Asn Glu Gln Cys Trp Phe Gly Lys
            35                  40                  45

Glu Ala Gly Asp Leu Val Asp Tyr Ile Tyr Gln Gly
        50                  55                  60

<210> SEQ ID NO 39
<211> LENGTH: 58
<212> TYPE: PRT
<213> ORGANISM: Mus musculus

<400> SEQUENCE: 39

Thr Leu Ile Val Met Ala Val Phe Thr Asp Glu Gln Arg Leu Arg Trp
1               5                   10                  15

Tyr Tyr Leu Leu Gly Trp Gly Phe Pro Ile Val Pro Thr Ile Ile His
            20                  25                  30

Ala Ile Thr Arg Ala Leu Tyr Tyr Asn Asp Asn Cys Trp Leu Ser Ala
            35                  40                  45

Glu Thr His Leu Leu Tyr Ile Ile His Gly
        50                  55

<210> SEQ ID NO 40
<211> LENGTH: 58
<212> TYPE: PRT
<213> ORGANISM: Rattus rattus

<400> SEQUENCE: 40

Thr Leu Ile Val Met Ala Val Phe Thr Glu Asp Gln Arg Leu Arg Trp
1               5                   10                  15

Tyr Tyr Leu Leu Gly Trp Gly Phe Pro Ile Val Pro Thr Ile Ile His
            20                  25                  30

Ala Ile Thr Arg Ala Val Tyr Tyr Asn Asp Asn Cys Trp Leu Ser Thr
            35                  40                  45

Glu Thr His Leu Leu Tyr Ile Ile His Gly
        50                  55

<210> SEQ ID NO 41
<211> LENGTH: 58
<212> TYPE: PRT
<213> ORGANISM: Homo sapiens

<400> SEQUENCE: 41

Thr Leu Ile Val Val Ala Val Phe Thr Glu Lys Gln Arg Leu Arg Trp
1               5                   10                  15

Tyr Tyr Leu Leu Gly Trp Gly Phe Pro Leu Val Pro Thr Thr Ile His
            20                  25                  30

Ala Ile Thr Arg Ala Val Tyr Phe Asn Asp Asn Cys Trp Leu Ser Val
            35                  40                  45

Glu Thr His Leu Leu Tyr Ile Ile His Gly
        50                  55

<210> SEQ ID NO 42
<211> LENGTH: 58
<212> TYPE: PRT
<213> ORGANISM: Mus musculus

```
<400> SEQUENCE: 42

Thr Leu Ile Val Val Ala Val Phe Ala Glu Lys Gln His Leu Met Trp
1               5                   10                  15

Tyr Tyr Phe Leu Gly Trp Gly Phe Pro Leu Leu Pro Ala Cys Ile His
            20                  25                  30

Ala Ile Ala Arg Ser Leu Tyr Tyr Asn Asp Asn Cys Trp Ile Ser Ser
        35                  40                  45

Asp Thr His Leu Leu Tyr Ile Ile His Gly
    50                  55

<210> SEQ ID NO 43
<211> LENGTH: 58
<212> TYPE: PRT
<213> ORGANISM: Rattus rattus

<400> SEQUENCE: 43

Thr Leu Ile Val Val Ala Val Phe Ala Glu Lys Gln His Leu Met Trp
1               5                   10                  15

Tyr Tyr Phe Leu Gly Trp Gly Phe Pro Leu Leu Pro Ala Cys Ile His
            20                  25                  30

Ala Ile Ala Arg Ser Leu Tyr Tyr Asn Asp Asn Cys Trp Ile Ser Ser
        35                  40                  45

Asp Thr His Leu Leu Tyr Ile Ile His Gly
    50                  55

<210> SEQ ID NO 44
<211> LENGTH: 58
<212> TYPE: PRT
<213> ORGANISM: Homo sapiens

<400> SEQUENCE: 44

Thr Leu Ile Val Val Ala Val Phe Ala Glu Lys Gln His Leu Met Trp
1               5                   10                  15

Tyr Tyr Phe Leu Gly Trp Gly Phe Pro Leu Ile Pro Ala Cys Ile His
            20                  25                  30

Ala Ile Ala Arg Ser Leu Tyr Tyr Asn Asp Asn Cys Trp Ile Ser Ser
        35                  40                  45

Asp Thr His Leu Leu Tyr Ile Ile His Gly
    50                  55
```

STABLE PROTEINS

RELATED APPLICATIONS

This application is a national stage filing under 35 U.S.C. § 371 of international application PCT/GB2012/051940, entitled "Stable Proteins," filed Aug. 9, 2012, which was published under PCT Article 21(2) in English, and claims the benefit under 35 U.S.C. § 119 of U.S. provisional application 61/522,147, entitled "Stable Proteins," filed Aug. 10, 2011, the entire contents of each of which is incorporated by reference herein in its entirety.

The invention relates to proteins that are not readily crystallisable and particularly to GPCRs that are not readily stabilised and therefore not readily crystallised. The invention also relates to methods for crystallising such proteins and various uses of them. The proteins are useful for drug discovery and development studies.

GPCRs constitute a very large family of proteins that control many physiological processes and are the targets of many effective drugs. Reference is made particularly to Overington et al (2006) *Nature Rev. Drug Discovery* 5, 993-996 which indicates that over a quarter of present drugs have a GPCR as a target. They are of considerable pharmacological importance. A list of GPCRs is given in Foord et al (2005) *Pharmacol Rev.* 57, 279-288, which is incorporated herein by reference.

GPCRs are generally unstable when isolated, and despite considerable efforts, it has only been possible to crystallise a few GPCRs including bovine rhodopsin, which naturally is exceptionally stable and the beta 2 adrenergic receptor which was crystallised as a fusion protein or in complex with an antibody fragment.

GPCRs are thought to exist in multiple distinct conformations which are associated with different pharmacological classes of ligand such as agonists and antagonists, and to cycle between these conformations in order to function (Kenakin T. (1997) *Ann N Y Acad Sci* 812, 116-125). Switching between conformations also contributes to the difficulty in obtaining crystal structures of receptors.

Based on sequence homology and molecular architecture, GPCRs can be classified into three families (A, B and C), although they all share the characteristic seven transmembrane (TM) domain. Family A, the largest group, consists of receptors that are homologous to Rhodopsin. Family B, also referred to as Secretin receptor family, are receptors that are regulated by large peptides hormones such as the glucagon hormone family; the members of this family are characterised by a relatively large extracellular N-terminus which contains several cysteines that form a network of disulphide bridges and is part of the ligand binding pocket. Family C consists of receptors that are homologous to metabotropic glutamate receptors; these receptors are characterised by a very long extra-cellular N-terminus as well as a long carboxy-tail, and the N-terminus forms the ligand binding pocket that has been shown to form a disulphide linked dimer, resembling a Venus fly trap in its shape.

Over the last few years the structure of a number of Family A GPCRs has been solved, and these milestones have been achieved by developing a number of key techniques. One such technology is the insertion of T4 lysozyme (T4L) in the intracellular cytoplasmic loop (ICL) 3, which is thought to create a large hydrophilic area that allows crystal contacts to form [2] [3]. The application of this technology in combination with Lipidic Cubic Phase crystallography has allowed high resolution structure determination of Beta2, A2a, CXCR4 and D3 receptors [2]. Thus, significant information has been gleaned from these structures about the orientation and organisation of the TM bundle of Family A receptors. However, little information is available for the members of Family B and C receptors and given the high sequence divergence, it is likely that significant differences exist in the architecture and organisation of the TM domains between families [1].

In Family A receptors, T4L was inserted in the ICL3 because it is thought that the distance between helices 5 and 6 is similar to the distance between the N- and C-termini of T4L. It is thus possible to accommodate the fusion protein in this position, whereas the distances between other helices are not believed to be conducive to the insertion of a fusion partner. Indeed, T4L has been fused to a number of different Family A receptors in ICL3 and functional protein has been expressed in each case with the added benefit of reducing the flexibility of the receptor, thus increasing overall stability.

We tested the effect of inserting T4L in the internal loops of Family B receptors and particularly in ICL3. Our data indicate that Family B receptors cannot tolerate T4L fusion in ICL3, however, surprisingly and unexpectedly, in view of the architecture of Family A receptors, adding T4L to ICL2 improves the biochemical properties of Family B receptors. ICL2 connects the portion of the GPCR comprising transmembrane helix (TM)-1, TM2 and TM3 to the portion of the GPCR comprising TM4, TM5, TM6 and TM7. The present data suggests that unlike Family A receptors, the distance between helices 3 and 4 in Family B receptors is more similar to the distance between the N- and C-termini of T4L, than is the distance between helices 5 and 6. Thus, insertion of a stable protein domain between these two portions of a GPCR is believed to represent a new technique for facilitating crystallisation of GPCRs that could not have been previously predicted.

Accordingly, a first aspect of the invention provides a fusion protein comprising, from N-terminus to C-terminus:
  a) a first portion of a Family B G-protein coupled receptor (GPCR) that comprises TM1, TM2 and TM3 of the GPCR;
  b) a stable protein domain; and
  c) a second portion of the GPCR comprising TM4, TM5, TM6 and TM7 of the GPCR.

By "GPCR" we mean a G protein coupled receptor or polypeptide that has the signalling activity of a GPCR and retains an intact 7TM region. Standard nomenclature in the art designates the transmembrane helices of a GPCR from N-terminus to C-terminus as TM1, TM2, TM3, TM4, TM5, TM6 and TM7. The transmembrane helices are joined by stretches of amino acids extracellularly between TM2 and TM3, between TM4 and TM5, and between TM6 and TM7, referred to as extracellular loop (ECL)s 1, 2 and 3, respectively. The transmembrane helices are joined by stretches of amino acids intracellularly between TM1 and TM2, between TM3 and TM4, and between TM5 and TM6, referred to as intracellular loop (ICL)s 1, 2 and 3, respectively. Thus, the first and second GPCR portions as defined above are naturally joined by the ICL2 region, i.e. ICL2 connects the first portion N-terminal to ICL2 comprising TM1, TM2 and TM3 to the second portion C-terminal to ICL2 comprising TM4, TM5, TM6 and TM7.

The GPCR is preferably derived from full length wild type sequences including natural polymorphisms or mutant GPCR molecules that have been altered, for example so as to improve one or more properties of the GPCR eg stability.

The GPCR may be derived from wildtype and mutant GPCRs wherein mutant GPCRs may be stabilised GPCRs biased towards a particular conformation such as agonist or antagonist. For example, a stable protein domain may then be inserted between TM3 and TM4 of a conformationally stabilised GPCR.

We have previously developed a methodology for the stabilisation of a GPCR in a biologically relevant conformation (see WO 2008/114020) describing the production of stabilised GPCRs known as StaRs™ that enables the purification of recombinant G protein coupled receptors that maintain their conformation, stability and function when purified from the cell membrane. In addition, this platform technology also provides the means to engineer receptors biased either towards agonist conformation or the antagonist conformation (see also Magnani et al, 2008; Serrano-Vega et al, 2008; Shibata et al, 2009), i.e. they have increased stability in a particular conformation. Such stabilised receptors may be used in the present invention and have a number of advantages, for example stability, elevated yields of purified protein, reduced denaturation and reduced nonspecific binding. Where a stable mutant GPCR is used in the present invention it is preferably selected and prepared using any of the methods as described in PCT applications WO 2008/114020, WO 2009/114020 and WO 2009/081136. Preferably the first and second GPCR portions are from a GPCR which has increased stability in a particular conformation relative to a parent GPCR (i.e. increased conformation stability). By increased conformational stability we include the meaning that a particular conformation of a mutant GPCR has, compared to the same conformation of the parent GPCR, increased stability (eg an extended lifetime) when exposed to a denaturant or denaturing conditions. Examples of denaturants/denaturing conditions include heat, detergent, a chaotropic agent and an extreme of pH. As is well known in the art, such denaturants or denaturing conditions can affect secondary and tertiary structures of a protein but not the primary sequence.

Suitable GPCRs for use in the practice of the invention include any Family B GPCR such as any of a glucagon-like peptide 1 receptor (GLP1R), glucagon-like peptide 2 receptor (GLP2R), calcitonin receptor (CT), amylin/CGRP receptor (AMY$_1$α), amylin receptor (AMY$_2$α), amylin/CGRP receptor (AMY$_3$α), CGRP/adrenomedullin receptor (CGRP$_1$α), adrenomedullin/CGRP receptor (AM$_1$α), adrenomedullin/CGRP receptor (AM$_2$α receptor), corticotropin releasing factor receptor (CRF$_1$), urocortins receptor (CRF$_2$), growth hormone releasing hormone receptor (GHRH), gastric inhibitory polypeptide receptor (GIP), glucagon receptor, secretin receptor, TIP-39 receptor (PTH2), parathyroid hormone receptor (PTH1), VIP/PACAP receptor (VPAC$_1$), PACAP receptor (PAC$_2$) and VIP/PACAP receptor (VPAC$_2$). In a particularly preferred embodiment, the GPCR is GLP1R. Other suitable GPCRs are well known in the art and include those listed in Overington et al supra. In addition, the International Union of Pharmacology produce a list of GPCRs that includes Family B GPCRs (Foord et al (2005) *Pharmacol. Rev.* 57, 279-288, and this list is periodically updated at http://www.iuphar-db.org/GPCR/ReceptorFamiliesForward; Family B GPCRs are listed in Table 2 as Class 2 GPCRs).

The amino acid sequences (and the nucleotide sequences of the cDNAs which encode them) of many GPCRs are readily available, for example by reference to GenBank. In particular, Foord et al supra gives the human gene symbols and human, mouse and rat gene IDs from Entrez Gene (http://www.ncbi.nlm.nihdov/entrez). It should be noted, also, that because the sequence of the human genome is substantially complete, the amino acid sequences of human GPCRs can be deduced therefrom.

Although the GPCR may be derived from any source, it is particularly preferred if it is from a eukaryotic source. It is particularly preferred if it is derived from a vertebrate source such as a mammal. It is particularly preferred if the GPCR is derived from rat, mouse, rabbit or dog or non-human primate or man. For the avoidance of doubt, we include within the meaning of "derived from" that a cDNA or gene was originally obtained using genetic material from the source, but that the protein may be expressed in any host cell subsequently. Thus, it will be plain that a eukaryotic GPCR (such as an avian or mammalian GPCR) may be expressed in a prokaryotic host cell, such as *E. coli*, but be considered to be avian- or mammalian-derived, as the case may be.

In some instances, the GPCR may be composed of more than one different subunit. For example, the calcitonin gene-related peptide receptor requires the binding of a single transmembrane helix protein (RAMP1) to acquire its physiological ligand binding characteristics. Effector, accessory, auxiliary or GPCR-interacting proteins which combine with the GPCR to form or modulate a functional complex are well known in the art and include, for example, receptor kinases, G-proteins and arrestins (Bockaert et al (2004) *Curr Opinion Drug Discov and Dev* 7, 649-657). In some instances, the GPCR may be bound to a GPCR ligand. By "ligand" we include any molecule which binds to the GPCR. Many ligands are known, for example from WO 2008/114020 and Neubig et al (2003) *Pharmacol. Rev.* 55, 597-606, both of which are incorporated herein by reference. Thus, the fusion protein may comprise a portion of the GPCR comprising TM1, TM2 and TM3 connected to a portion of the GPCR comprising TM4, TM5, TM6 and TM7, wherein the GPCR is bound to a GPCR binding partner. In this way, it is possible to gain structural insights into GPCR interactions by being able to crystallise complexes of GPCR with other molecules. It is preferred if the molecules are not ones that bind to ICL2 of the GPCR.

For any given GPCR, the TM helices can be determined by the skilled person using standard techniques in the art. For example, computer programs are available which model transmembrane regions of GPCRs based on hydrophobicity (Kyle & Dolittle (1982) *J. Mol. Biol.* 157, 105-132). Likewise transmembrane prediction algorithm servers are widely available on the World Wide Web (eg Expasy), many of which rely on hydropathy analysis. TMHMM is a membrane protein topology prediction method that may be used, based on a hidden Markov model (TMHMM Server v. 2.0; http://www.cbs.dtu.dk/services/TMHMM/). Where the transmembrane regions are already known for a given GPCR, for example by structural analysis or hydropathy analysis, the analogous regions in a further GPCR can also be identified by multiple or pairwise sequence alignment. For example, the alignment may be carried out using the Clustal W program (Thompson et al., 1994). The parameters used may be as follows: Fast pairwise alignment parameters: K-tuple (word) size; 1, window size; 5, gap penalty; 3, number of top diagonals; 5. Scoring method: x percent. Multiple alignment parameters: gap open penalty; 10, gap extension penalty; 0.05. Scoring matrix: BLOSUM.

FIG. 6 lists the amino acid sequences of Family B GPCRs and highlights the position of TM3, ICL2 and TM4. For example, for human GLP1R, TM3 ends with Phe 257, ICL2 corresponds to Ser 258 to Ser 261, and TM4 begins with Glu 262. Conveniently therefore, when the GPCR is a Family B receptor, the positions of TM3, ICL2 and TM4 can be identified by locating the amino acid residues that correspond to the amino acids that define the boundaries of TM3, ICL2 and TM4 in FIG. 6, when the sequences are aligned, for instance using CLUSTAL W.

It will be appreciated, however, that the boundaries are not absolute and they may well depend on the model provided for GLP1R that has been used to define them. In FIG. 1, for example, TM3 of human GLP1R ends with Leu 254, ICL2 corresponds to Leu 255 to Trp 264, and TM4 begins with Ile 265. Also, the loop regions may be defined as amino acid structures that join alpha helices or amino acid structures that are predicted to be outside the membrane, and depending on which definition is used, the boundaries will change.

In one embodiment, the stable protein domain is inserted into ICL2. Thus, the invention provides a GPCR into which a stable protein domain has been inserted into ICL2. By 'inserted into ICL2' we include both the addition of the amino acid sequence that defines the stable protein domain into the amino acid sequence of ICL2 without the deletion of any amino acids of ICL2, and also the replacement of one or more or all amino acids of ICL2 with the amino acid sequence encoding the stable protein domain. It will be appreciated that in this embodiment, the first and/or second portion of the GPCR may comprise at least part of ICL2, in addition to the requisite transmembrane helices. The first portion of the GPCR may comprise TM1, TM2 and TM3 and an N-terminal part of ICL2. The second portion of the GPCR may comprise TM4, TM5, TM6 and TM7 and a C-terminal part of ICL2.

It is appreciated that the stable protein domain may be inserted into ICL2 and flanked by one or two spacer moieties at its N- and/or C-terminus. In this way, the stable protein domain is not directly linked to ICL2 but is indirectly linked. The spacer moieties may be used to help reduce tension on the helices.

Preferably, the stable protein domain is inserted into ICL2 by replacing one or more consecutive amino acids (eg 2, 3, 4 or 5 or more amino acids) in the amino acid sequence of ICL2 with the amino acid sequence of the stable protein domain. In one embodiment, the one or more amino acids that are replaced is/are at least one or two amino acids from the C-terminus of TM3 and/or the N-terminus of TM4. In other words, the fusion protein may have at least one or two amino acids of ICL2 on at least one of the sides of the stable protein domain.

As described in Example 1, we have inserted T4 lysozyme at various positions in ICL2 of GLP1R, and insertions between Phe 257 and Ser 261 resulted in productive fusion GLP1R receptors. Thus, it is particularly preferred that the stable protein domain is inserted into the ICL2 region of the GPCR at a position between amino acid residues that correspond to amino acids Phe 257 and Ser 261 according to the numbering of human GLP1R as set out in FIG. 6.

Accordingly, the amino acid of the stable protein domain may be inserted into the ICL2 region of the GPCR after an amino acid corresponding to amino acid Phe 257 and before an amino acid corresponding to amino acid Ser 261 or Phe 260 or Val 259, according to the numbering of human GLP1R as set out in FIG. 6. For example, the amino acid sequence of the stable protein domain may replace the amino acid corresponding to Ser 258, or it may replace amino acids corresponding to Ser 258 and Val 259, or it may replace amino acids corresponding to Ser 258, Val 259 and Phe 260, according to the numbering of human GLP1R as set out in FIG. 6. Inserting the stable protein domain at such positions corresponds to the GLP1R-T4 lysozyme fusion constructs 1c, 2c and 3c shown in FIG. 1.

Similarly, the amino acid of the stable protein domain may be inserted into the ICL2 region of the GPCR after an amino acid corresponding to amino acid Ser 258 and before an amino acid corresponding to amino acid Ser 261 or Phe 260 or Val 259, according to the numbering of human GLP1R as set out in FIG. 6. For example, the amino acid sequence of the stable protein domain may replace the amino acid corresponding to Val 259, or it may replace amino acids corresponding to Val 259 and Phe 260, according to the numbering of human GLP1R as set out in FIG. 6. Inserting the stable protein domain at such positions corresponds to the GLP1R-T4 lysozyme fusion constructs 1d, 2d and 3d shown in FIG. 1.

By "corresponding amino acid residue" we include the meaning of the amino acid residue in another GPCR that aligns to the given amino acid residue in human GLP1R when the human GLP1R receptor and the other GPCR are compared using MacVector and CLUSTALW.

Although it is preferred that the stable protein domain is inserted into the ICL2 region of the GPCR at a position between amino acid residues that correspond to amino acids Phe 257 and Ser 261 according to the numbering of human GLPIR as set out in FIG. 6, it is appreciated that it may be inserted outside of this region.

It is appreciated that the function of the stable protein domain is to increase the hydrophilic surface for crystal contacts and to reduce the inherent flexibility of GPCRs in order to, for example, improve the crystallisation properties of the GPCR. Accordingly, by 'stable protein domain' we include the meaning of any soluble, folded polypeptide that provides a hydrophilic surface for crystal lattice contacts. Further, the protein domain is stable such that in its folded form it is resistant to denaturation (eg is stable to heat, detergents and chaotropic agents etc.). Tests for protein stability are well known in the art and include those described in WO2008/114020.

Typically, the stable protein domain is one that folds autonomously from the GPCR portions of the fusion protein in the cell.

Conveniently, the stable protein domain is one that is readily crystallisable. Thus, the stable protein domain may be a protein whose crystal structure has been solved, for example one whose coordinates has been deposited in the Protein Data Bank (http://www.pdb.org/).

Particularly preferred characteristics of the stable protein domain are:
1. the domain is soluble, well folded and can be expressed easily in one or more expression systems;
2. the N- and C-termini of the domain are close together in space; typically in the range of 5-17 Å eg 6-16 Å, 7-15 Å, 7-10 Å, 10-13 Å or 12-15 Å;
3. the domain is resistant to thermal and chemical denaturation as well as to proteolytic degration;
4. the domain is highly crystallisable in a variety of space groups and crystal packing arrangements.

It is preferred that the domain does not contain cysteine residues so as to prevent disulphide bond formation either within the domain or with the GPCR portion of the fusion protein. It will be understood that since the domain is soluble it should not be hydrophobic or have the propensity to aggregate in a disordered fashion.

In one embodiment, the length of the stable protein domain is between 50 and 1000 amino acids, preferably between 50 and 300 amino acids or 100 and 300 amino acids, or between 150 and 250 amino acids.

Once a suitable polypeptide has been found for the stable protein domain, it may be necessary to modify the polypeptide by deleting or adding amino acid residues from or to the N-terminus, the C-terminus or both termini of the polypeptide such that the closest alpha carbon atoms in the backbone at the termini of the polypeptide are spaced by a distance of in the range of 5-17 Å eg 6-16 Å, 7-15 Å, 7-10 Å, 10-13 Å or 12-15 Å.

It is preferred if insertion of the stable protein domain does not affect a biological activity of the GPCR, such as a binding activity or a signalling pathway modulation activity. Ideally, the fusion protein should retain at least 60% or 70% or 80% or 90% of its biological activity, and most ideally 100% of its biological activity relative to the level of the same activity in the absence of the stable protein domain. Methods for assessing GPCR binding and GPCR signalling are well known in the art and are described for example in WO 2008/114020 and WO 2009/101383, both of which are incorporated herein by reference. Thus, where the biological activity is a binding activity, binding to any GPCR binding partner may be assessed using routine binding assays known in the art; where the biological activity is a signalling pathway modulating activity, the activity can be assessed by any suitable assay for the particular signalling pathway (eg reporter gene assays).

It is appreciated that retaining ligand binding ability is more important for crystallisation purposes than is retaining signalling activity, and that it may be desirable to only assess ligand binding ability prior to crystallisation. Thus in a particularly preferred embodiment, the stable protein domain does not affect a binding activity of a GPCR.

For the avoidance of doubt, the stable protein domain is not ICL2 or part thereof of the particular GPCR.

In a preferred embodiment, the stable protein domain is lysozyme. Lysozyme is known to be readily crystallisable and the structures of various wild type and variant lysozymes have been deposited in the Protein Data Bank (www.rcsb.org). Suitable examples include 135L, 193L, 194L, 1AKI, 1GBS, 1IEE, 1LZ1, 1P7S, 1REX, 1VDQ, 2ANV, 2ANX, 2D4K, 2FBB, 2IHL, 2NWD, 2XBR, 2XBS, 2Z2F, 2ZYP, 3A8Z, 3K2R, 3N9A, 3N9C, 3N9E and 3OD9

Although lysozyme derived from any source may be used, it is particularly preferred if the lysozyme is derived from T4 phage. Two amino acid sequences of T4 phage lysozyme are provided in FIG. 7, and either of the sequences may be used in the context of the invention. The lysozyme may be derived from full length wild type sequences including natural polymorphisms or it may be a mutant lysozyme that has been altered, for example to improve one or more properties. Thus, it is understood that variants of the amino acid sequences provided in FIG. 7 may be used, such as amino acid sequences with at least 60%, 65%, 70%, 75%, 80%, 85% or 90% sequence identity with either of the sequences set out in FIG. 7, and more preferably at least 95% or 99% sequence identity with either of the sequences set out in FIG. 7.

Sequence identity may be measured by the use of algorithms such as BLAST or PSI-BLAST (Altschul et al, NAR (1997), 25, 3389-3402) or methods based on Hidden Markov Models (Eddy S et al, J Comput Biol (1995) Spring 2 (1) 9-23). Typically, the percent sequence identity between two polypeptides may be determined using any suitable computer program, for example the GAP program of the University of Wisconsin Genetic Computing Group and it will be appreciated that percent identity is calculated in relation to polypeptides whose sequence has been aligned optimally. The alignment may alternatively be carried out using the Clustal W program (Thompson et al., 1994) as mentioned above.

While lysozyme is a preferred example of a stable protein domain, the general principles may be used to employ any number of polypeptides that have the characteristics discussed above. Thus, suitable candidates include those containing the amino acid sequence of proteins that are readily crystallisable, for example as found by interrogating the protein data bank or other crystallization databases known in the art. Other examples include those mentioned in Engel et al (2002) *BBA* 1564: 38-46 (incorporated herein by reference), such as cytochrome$_{b562}$, flavodoxin, β-lactamase and 70 kDa heat shock ATPase domain.

The fusion protein may be modified so that it can be more easily detected, for example by biotinylating it or by incorporating any detectable label known in the art such as radiolabels, fluorescent labels or enzymatic labels. In a particularly preferred embodiment, the label is a fluorescent label such as EGFP. Similarly, the fusion protein may be modified to facilitate purification, for example by incorporating any affinity moiety known in the art such as a GST tag, 6×His tag, MBP or other epitope tag. Such modifications may be at the N-terminus or C-terminus of the GPCR or in an external loop.

As demonstrated in Example 1, it is believed that the fusion proteins of the invention have improved biochemical properties compared to the biochemical properties of the GPCR without the insertion of the stable protein domain. Such improved properties make the fusion protein more amenable to crystallisation. Thus, the fusion protein is expected to have a larger hydrophilic surface for crystal contacts. Similarly, the fusion protein is expected to be more soluble, eg displaying less aggregation in detergent solution, than the GPCR without insertion of the stable protein domain. Methods for assessing GPCR solubility are well known in the art and include size exclusion chromatography such as fluorescent size exclusion chromatography used to assess solubility in DDM as described in Example 1. The fusion protein may also be more stable (eg to any of heat, detergent or chaotropic agents) than the GPCR without the insertion of the stable protein domain. Methods for assessing GPCR stability are known in the art, including those described in WO 2008/114020.

Conveniently, the fusion protein is produced by standard molecular biology and recombinant DNA techniques. For example, DNA fragments encoding the first and second GPCR portions and the stable protein domain may be made using standard cloning techniques and PCR as is well known in the art. The fragments can then be ligated together in-frame in accordance with conventional practice, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation.

Equally, the fusion constructs can be made using ligase independent cloning strategies such as InFusion or Gateway. The construct may also be made synthetically through de novo gene synthesis.

It is appreciated that one or both of the GPCR and stable protein domain may be mutated so as to improve any of solubility, stability, expression and crystallisability.

Molecular biological methods for cloning and engineering genes and cDNAs, for mutating DNA, and for expressing polypeptides from polynucleotides in host cells are well known in the art, as exemplified in "Molecular cloning, a laboratory manual", third edition, Sambrook, J. & Russell, D. W. (eds), Cold Spring Harbor Laboratory Press, Cold Spring Harbor, N.Y., incorporated herein by reference.

Suitable expression systems include constitutive or inducible expression systems in bacteria or yeasts, virus expression systems such as baculovirus, semliki forest virus and lentiviruses, or transient transfection in insect or mammalian cells. Suitable host cells include E. coli, Lactococcus lactis, Saccharomyces cerevisiae, Schizosaccharomyces pombe, Pichia pastoris, Spodoptera frugiperda and Trichoplusiani cells. Suitable animal host cells include HEK 293, COS, S2, CHO, NSO, DT40 and so on. It is known that some GPCRs require specific lipids (eg cholesterol) to function. In that case, it is desirable to select a host cell which contains the lipid. Additionally or alternatively the lipid may be added during isolation and purification of the fusion protein. Purification may be carried out by standard techniques such as affinity chromatography.

A second aspect of the invention provides a polynucleotide encoding the fusion protein according to the first aspect of the invention. The polynucleotide may be RNA (eg mRNA) or DNA, although typically it is DNA.

It will be appreciated that the polynucleotide may be incorporated into a vector, and so the invention also provides a vector comprising a polynucleotide according to the second aspect of the invention.

Suitable vectors are ones which propagate in and/or allow expression of the fusion protein in prokaryotic (eg bacterial) or eukaryotic (eg mammalian) cells. For example, the vector may be a plasmid, a cosmid, a phage or a bacterial artificial chromosome (BAC). The polynucleotide sequence of the vector will depend upon the nature of the intended host cell, the manner of the introduction of the polynucleotide of the second aspect of the invention into the host cell, and whether episomal maintenance or integration is desired. Conveniently, the vector comprises at least one selectable marker such as antibiotic resistance (eg kanamycin or neomycin).

Vectors are useful to replicate the polynucleotide of the second aspect of the invention, and are also useful to transfect cells with the polynucleotide, and may also promote expression of the fusion protein.

Typical prokaryotic vector plasmids are: pUC18, pUC19, pBR322 and pBR329 available from Biorad Laboratories (Richmond, Calif., USA); pTrc99A, pKK223-3, pKK233-3, pDR540 and pRIT5 available from Pharmacia (Piscataway, N.J., USA); pBS vectors, Phagescript vectors, Bluescript vectors, pNH8A, pNH16A, pNH18A, pNH46A available from Stratagene Cloning Systems (La Jolla, Calif. 92037, USA).

A typical mammalian cell vector plasmid is pSVL available from Pharmacia (Piscataway, N.J., USA). This vector uses the SV40 late promoter to drive expression of cloned genes, the highest level of expression being found in T-antigen-producing cells, such as COS-1 cells. Another example is pcDNA3.1 (neo) (Invitrogen) for use in COS-1 or COS-7 cells. An example of an inducible mammalian expression vector is pMSG, also available from Pharmacia (Piscataway, N.J., USA). This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems (La Jolla, Calif. 92037, USA). Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

In a preferred embodiment, the vector comprising the polynucleotide of the second aspect of the invention is pcDNA3.1 (http://products.invitrogen.com/ivgn/product/V79020).

Any suitable method known in the art may be used to construct vectors containing the polynucleotide of the second aspect of the invention including the ligation techniques described above.

A third aspect of the invention provides a cell comprising a polynucleotide according to the second aspect of the invention, or a vector comprising said polynucleotide. Such cells may be used to replicate the polynucleotide of the second aspect of the invention, or may be used to express the fusion protein of the first aspect of the invention.

The cell can be either prokaryotic or eukaryotic.

It is appreciated that construction and amplification of the polynucleotide of the second aspect of the invention is conveniently performed in bacterial cells. Expression of the polynucleotide may be carried out in cells such as mammalian cells or bacterial cells.

Bacterial cells are preferred prokaryotic host cells and typically are a strain of E. coli such as, for example, the E. coli strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells or cell lines, preferably vertebrate cells or cell lines such as those from a mouse, rat, monkey or human. Particularly preferred cells are human embryonic kidney cells such as HEK293T cells.

Cells used for expressing the fusion protein may be either stably or non-stably transfected.

A fourth aspect of the invention provides a method of crystallising a fusion protein according to the first aspect of the invention, the method comprising providing a fusion protein according to the first aspect of the invention and crystallising it to obtain crystals.

In an embodiment, the fusion protein is provided by culturing a host cell according to the third aspect of the invention to express the fusion protein and isolating the protein.

Any suitable crystallisation method may be used to crystallise the fusion protein, such as any of those reviewed in "Crystallisation of Biological Macromolecules" (Alexander McPherson; ISBN: 0-87969-617-6), which is incorporated herein by reference.

In a preferred embodiment, the crystallisation is carried out using lipidic cubic phase crystallography (see US 2011/0031438 incorporated herein by reference).

A fifth aspect of the invention provides a crystal comprising a fusion protein of the first aspect of the invention.

The fusion proteins disclosed herein are useful for crystallisation studies and are useful in drug discovery programmes. They may be used in biophysical measurements of receptor/ligand kinetic and thermodynamic parameters eg by surface plasmon resonance or fluorescence based techniques. They may be used in ligand binding screens, and may be coupled to solid surfaces for use in high throughput screens or as biosensor chips. Biosensor chips containing the fusion proteins may be used to detect molecules, especially biomolecules.

The invention will now be described with the aid of the following figures and examples.

FIGS. 1A and B. Design of T4L fusion constructs with GLP1R. T4L was inserted after the indicated residues in ICL2 (left) and ICL3 (right). Construct 1a means that T4L was inserted between L255 and S261. The model of TM domains and loops are based on reference [4].

FIG. 2. Total EGFP signal of GLP1R-T4L fusion constructs compared to the wild-type (WT) and the mock transfected (U) samples. Each measurement was done on 50 ug of total cellular material in duplicate. Error bars represent standard deviation from mean.

Figure 3:
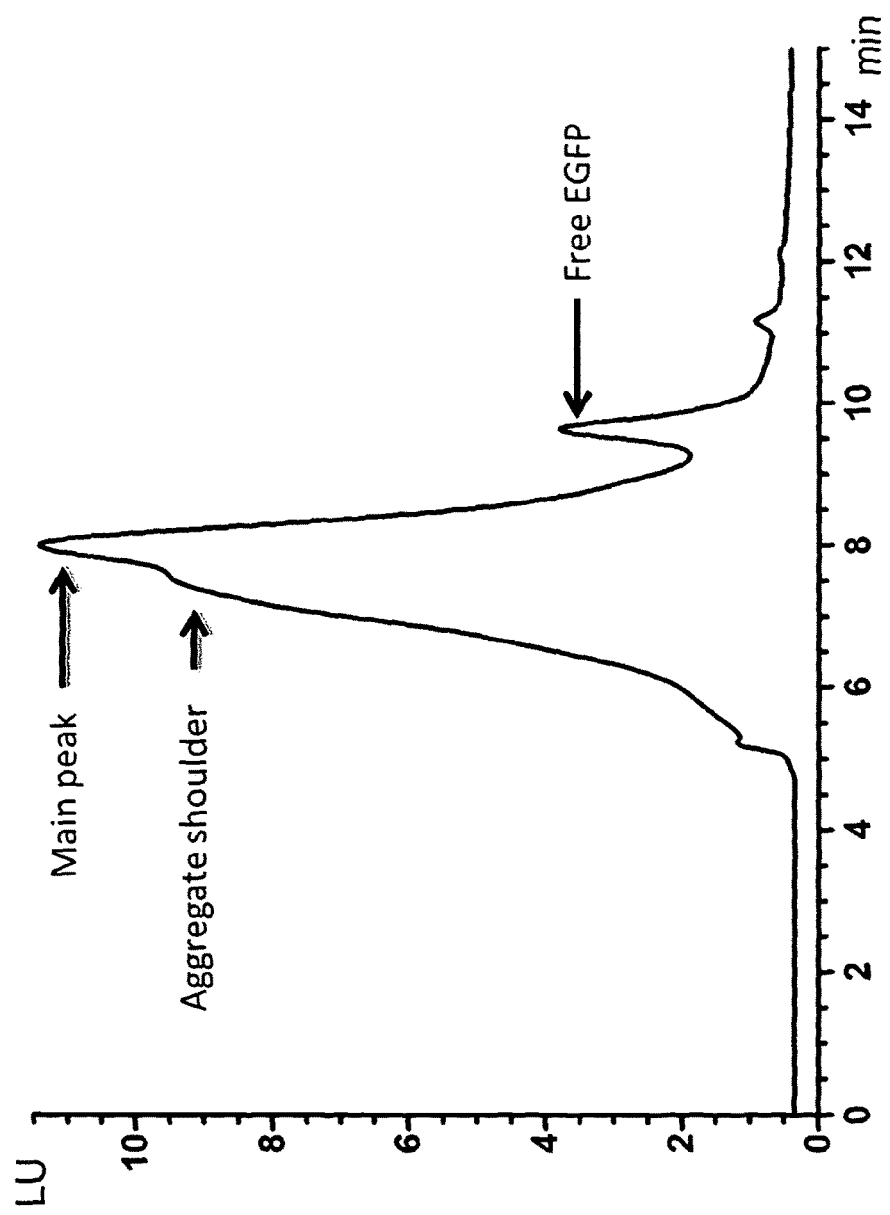

FIG. 3. Typical fSEC elution profile of wild-type GLP1R.

Figure 4C:
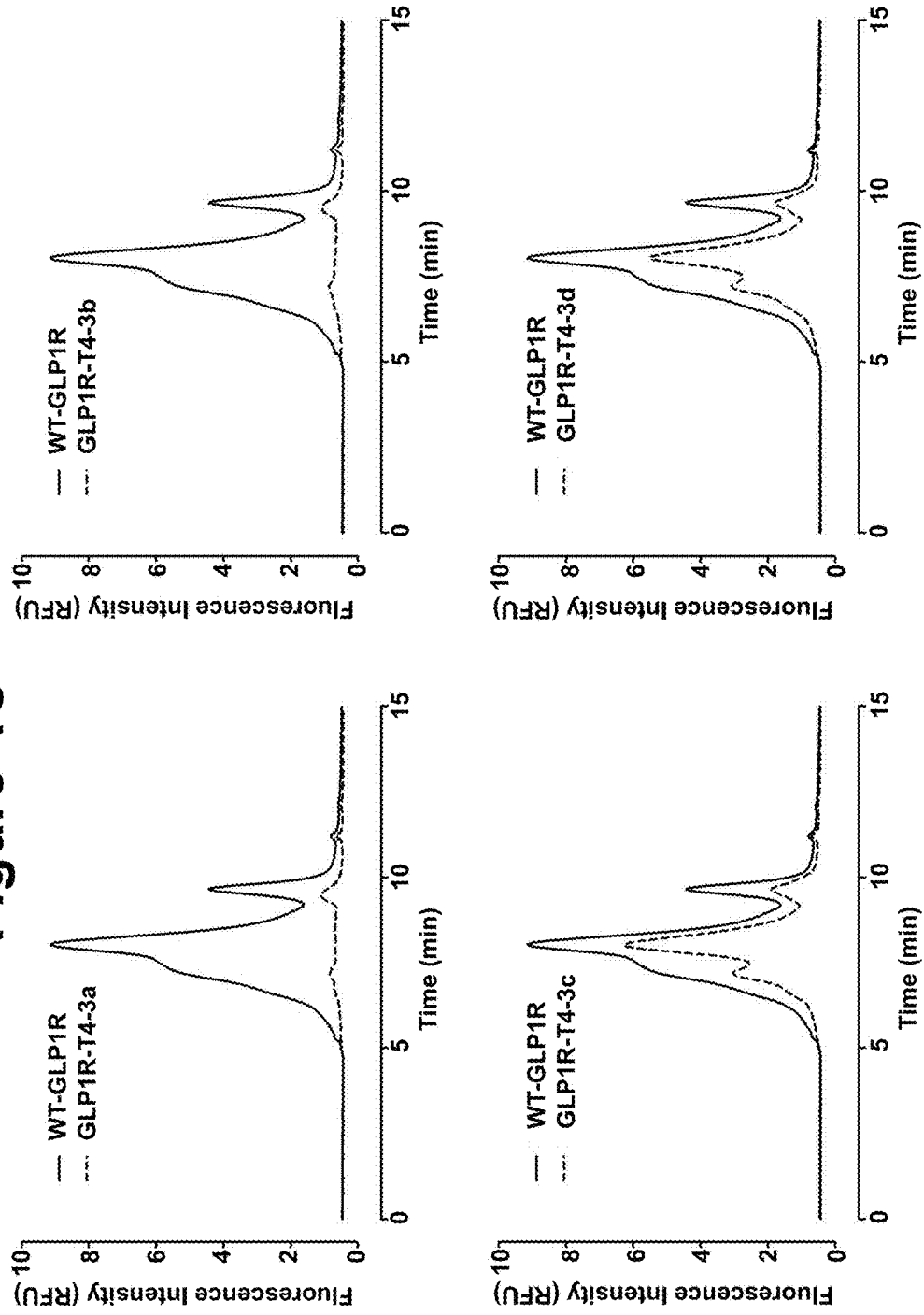
Figure 5A:
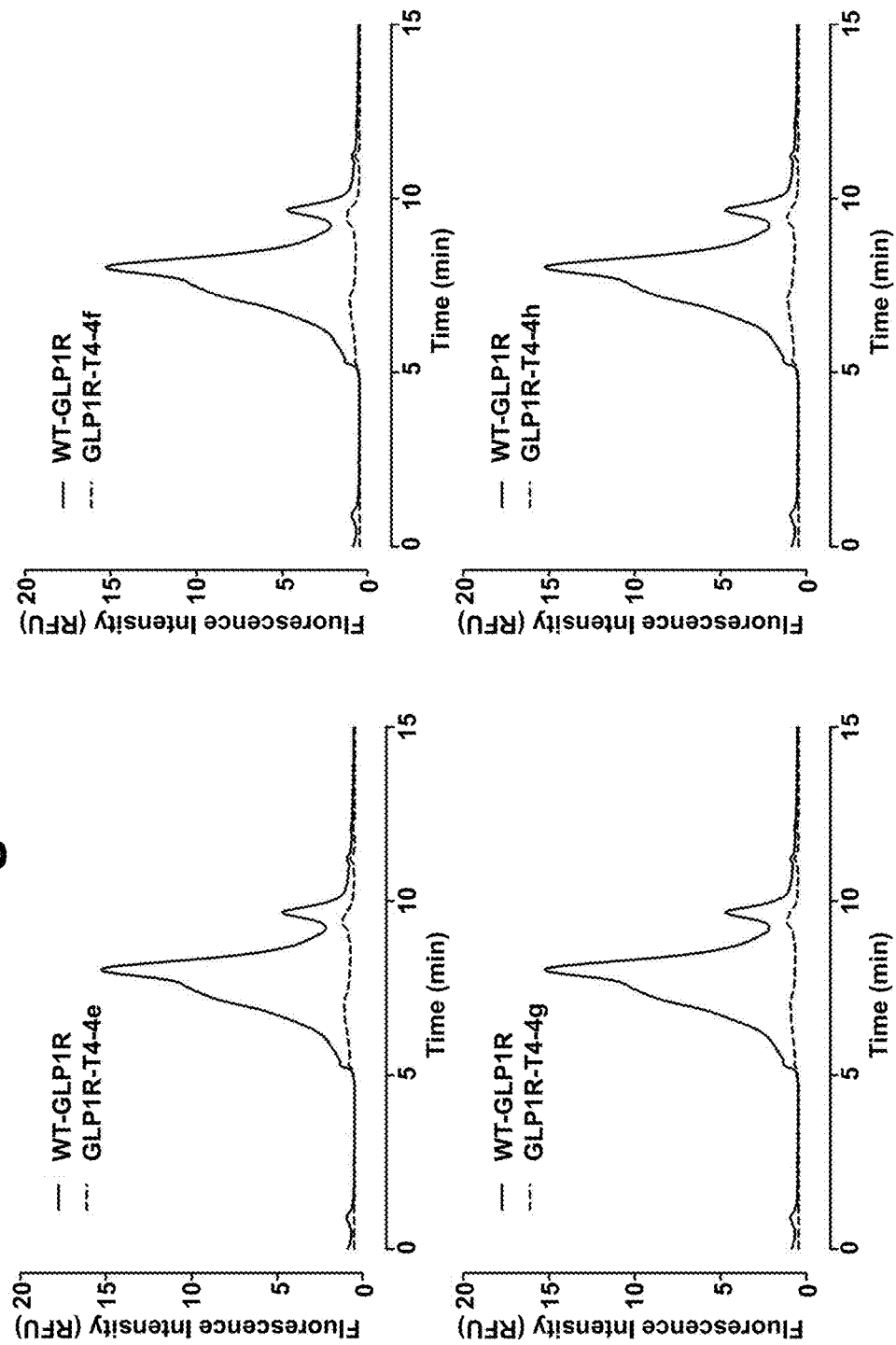
Figure 5B:
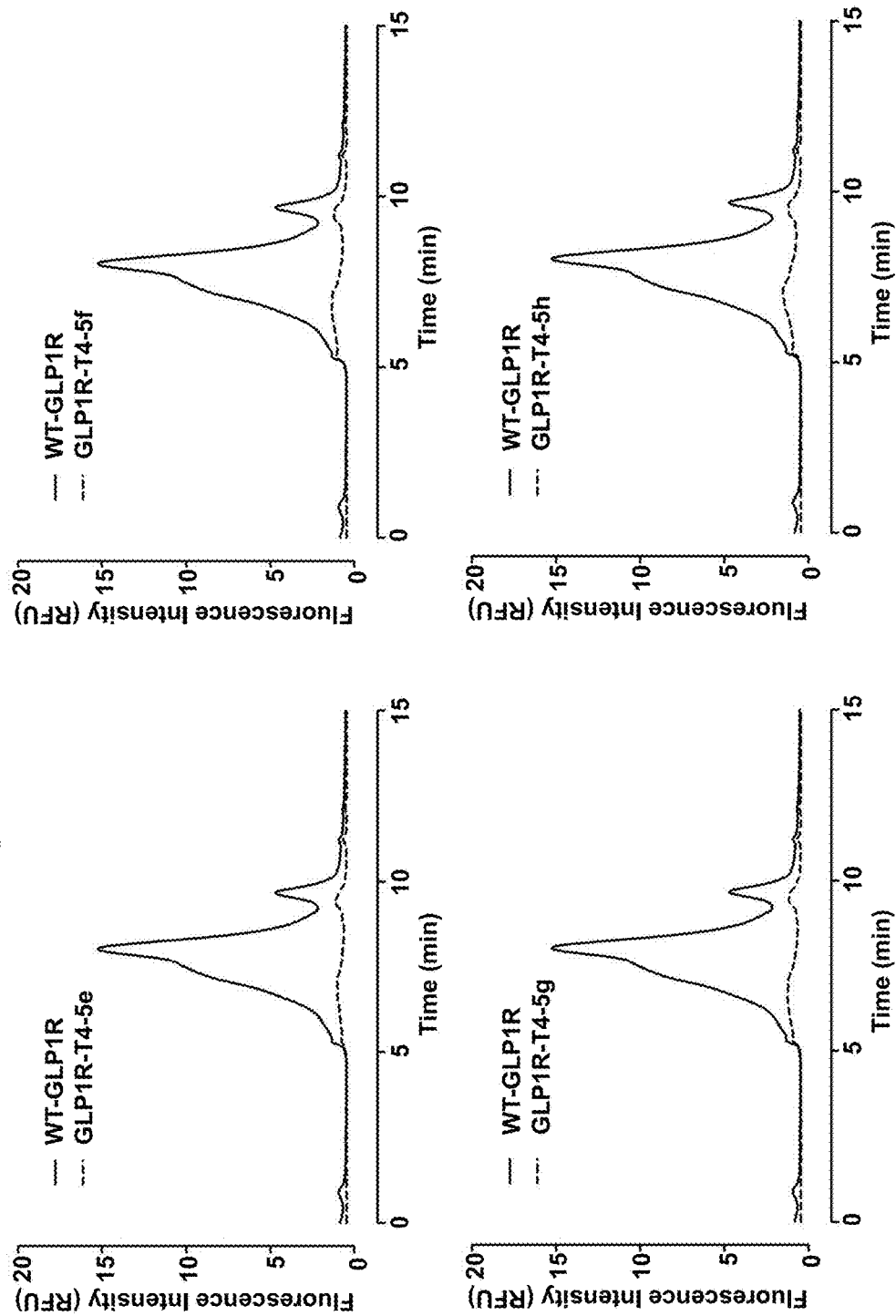
Figure 5C:
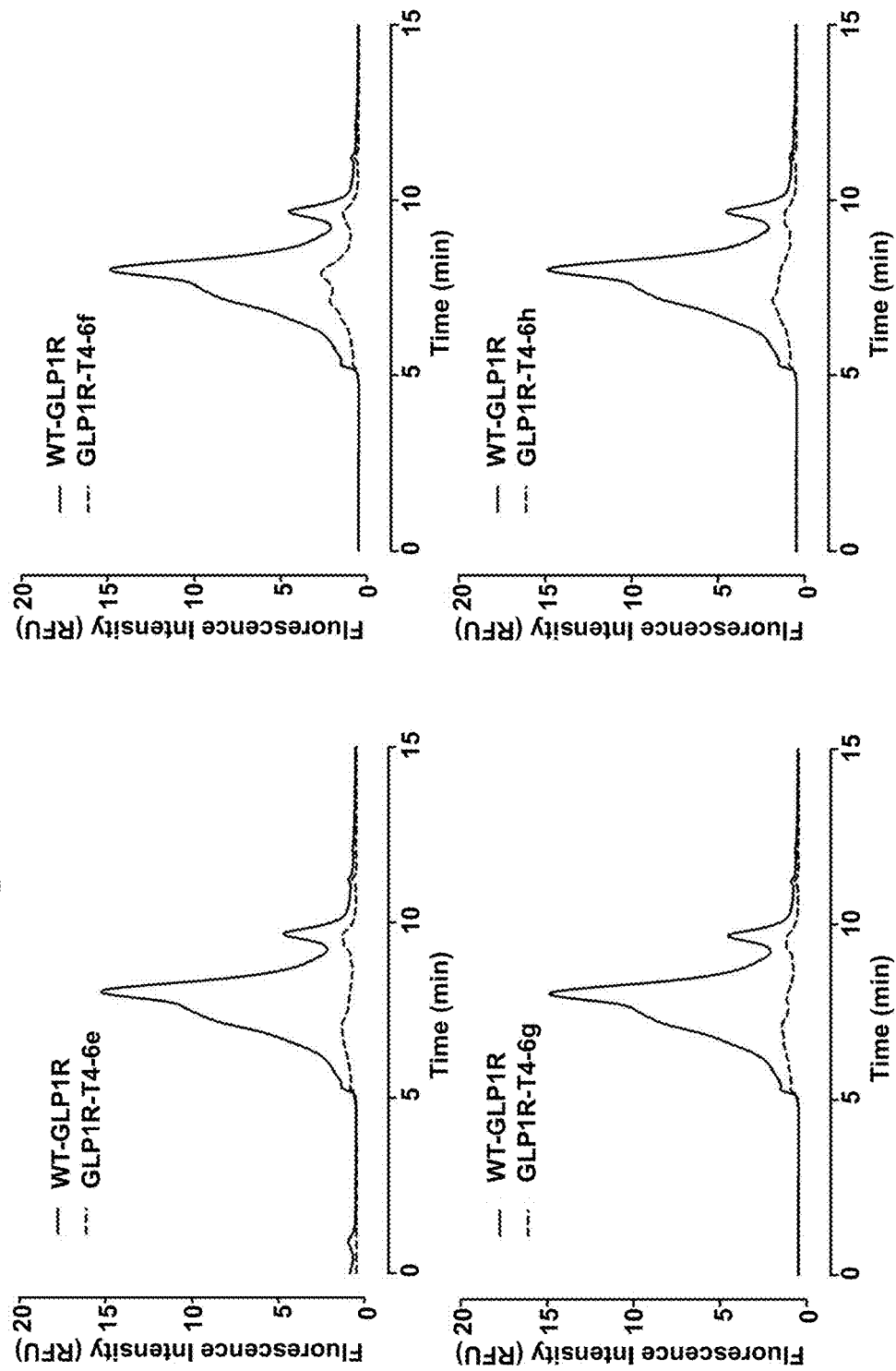
Figure 5D:
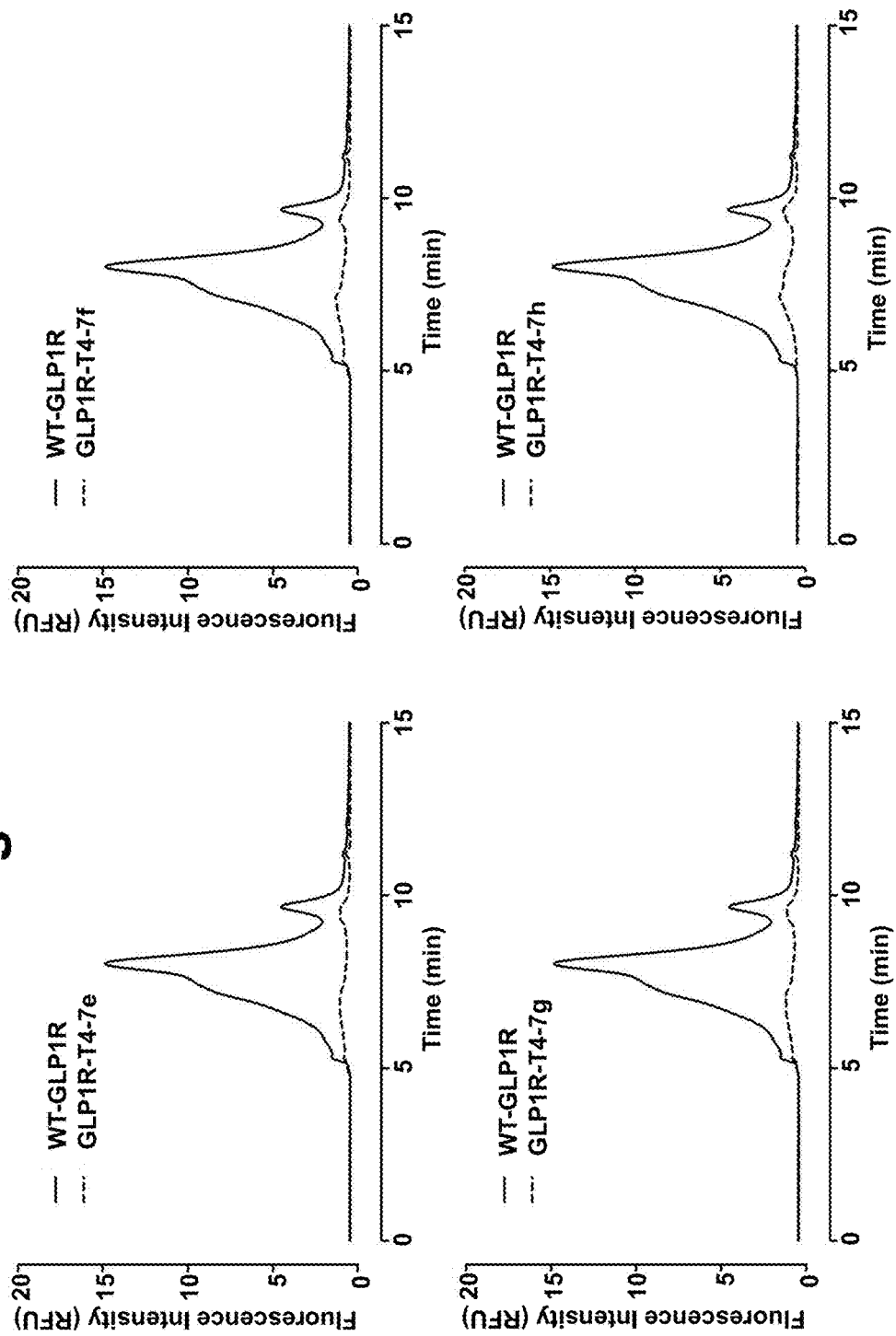
Figure 5E:
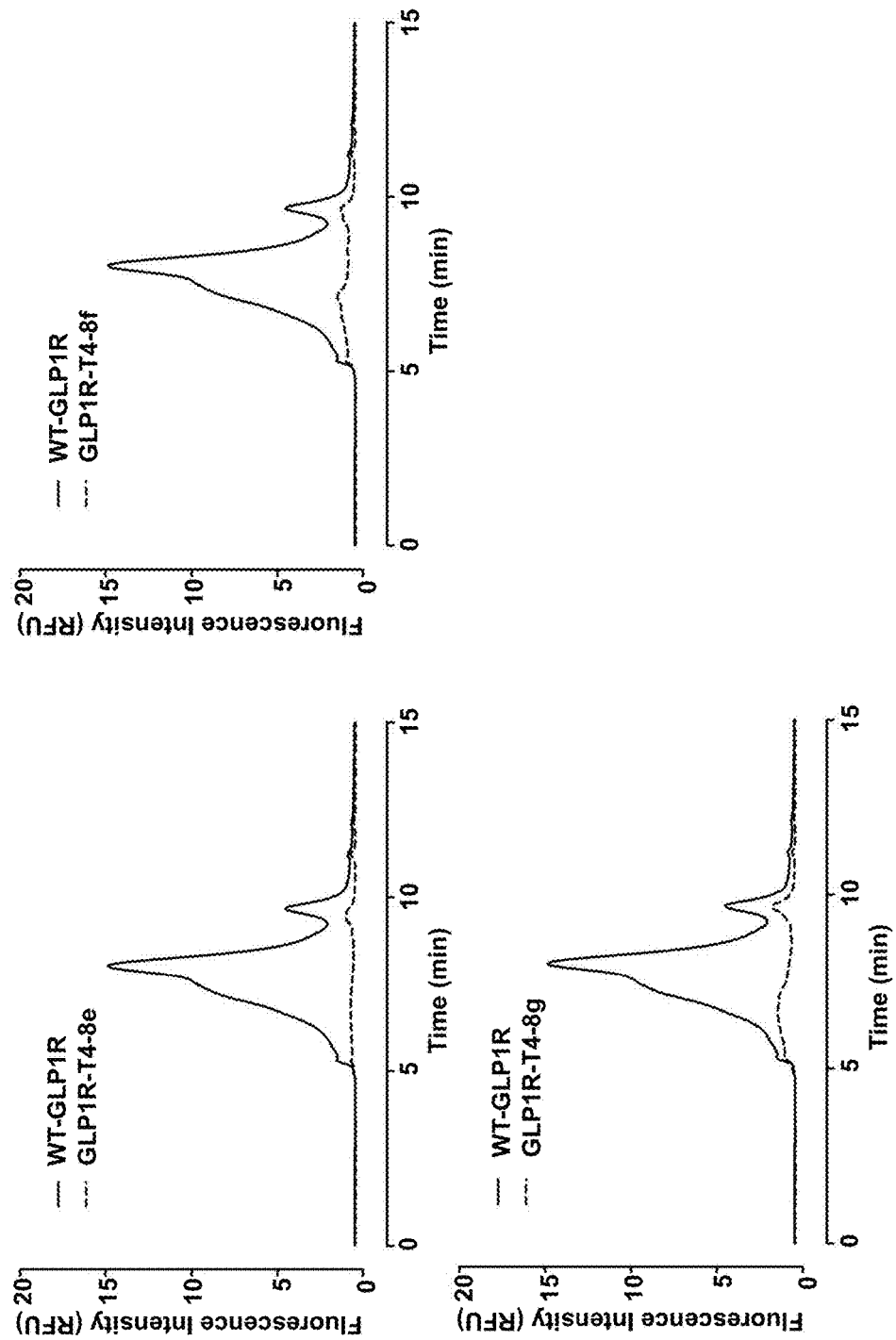

FIG. 4A-C. fSEC elution profiles DDM solubilised GLP1R-T4L fusion constructs in the ICL2 overlaid the wild-type profile. In each case, the wild-type profile is shown in red the fusion constructs in blue.

FIG. 5A-E. fSEC elution profiles DDM solubilised GLP1R-T4L fusion constructs in the ICL3 overlaid the wild-type profile. In each case, the wild-type profile is shown in red the fusion constructs in blue.

FIG. 6. Amino acid sequences of Family B GPCRs showing position of TM3, ICL2 and TM4 (SEQ ID Nos: 1-22). The portion of ICL2 that was replaced with T4L in GLP1R fusion construct 1c is highlighted in other Family B receptors from mouse, rat and human.

FIG. 7. Amino acid sequences of T4 phage lysozyme: (A) Sequence inserted into ICL3 of Family A receptors [2], [3] (SEQ ID No: 23); (B) Sequence inserted into ICL2 of Family B receptors (SEQ ID No: 24) (see Examples). Differences are indicated in boxes.

EXAMPLE 1: INSERTION OF T4L INTO ICL2 IMPROVES BIOCHEMICAL PROPERTIES OF GLP1R

Summary

We have tested the effect of inserting T4L in the internal loops of Family B receptors. Our data indicate that Family B receptors cannot tolerate T4L fusion in ICL3, however, adding T4L to ICL2 improves the biochemical properties of the receptor.

Results

The loop regions of GLP1R were determined according to the model of GLP1R and the DNA encoding T4L was inserted in different locations within ICL2 and ICL3 (FIG. 1). The GLP1R construct was C-terminally tagged with the EGFP in order to monitor total expression as well as monodispersity using fluorescent-detection size exclusion chromatography.

Following sequence confirmation, these constructs were expressed in HEK293T transiently. As an initial analysis, the EGFP signal in whole cells was measured to assess the total levels of expression. Interestingly, the constructs in ICL3 failed to produce any EGFP signal, indicating that T4L fusion in this region of GLP1R is incompatible with the overall architecture of this receptor. However, fusions in the ICL2 resulted in the robust expression of GLP1R (FIG. 2).

In order to analyse the biochemical properties of GLP1R-T4L fusions, cells expressing these constructs were solubilised in dodecyl maltoside (DDM) and applied to fluorescence-detection size-exclusion chromatography (fSEC). fSEC has been used widely to provide data regarding the monodispersity and the aggregation status of the proteins, particularly in pre-crystallisation screens [5]. In general, the more favourable conditions will result in more monodispersity and reduced aggregation. The fSEC elution profile of DDM-solubilised wild-type GLP1R shows the presence of the main monodispersed peak with an aggregation shoulder as well as free EGFP species that are the result of proteolytic degradation (FIG. 3).

Consistent with the EGFP signal data showed in FIG. 2, the elution profiles of ICL2 T4L fusion constructs 1a, 1b, 2a, 2b, 3a and 3b indicates that cells failed to express these fusions (FIG. 4). This is most likely due to the proximity of the N-terminus of T4L to TM III, leading to the disruption of the overall structure. In contrast, the elution profiles of constructs 1c, 1 d, 2c, 2d, 3c and 3d revealed that productive fusion receptors were expressed and more significantly it appears that T4L fusion results in the reduction of the aggregation peak and concomitant improvement of the monodispersed peak, which together indicate that T4L insertion in this region of the receptor has beneficial effect on the biochemical properties of solubilised receptor (FIG. 4). This effect is most pronounced in the constructs 1c and 2c.

The same analysis was carried out for the ICL3 fusion constructs and in agreement with the EGFP signal data showed in FIG. 2, none of the T4L fusions in the ICL3 resulted in the expression of any productive fusion receptor (FIG. 5).

Taken together, these data indicate that T4L fusion in the third cytoplasmic loop of GLP1R is not tolerated, however, insertion of T4L in certain positions in the second cytoplasmic loop not only is tolerated, it also improves the biochemical properties of the solubilised receptor. Given the high sequence homology amongst members of the Family B GPCRs, we suggest that these observations can be extended to other members of this Family. The portion of the ICL2 that was replaced in the best construct (1c) is highlighted in other Family B members as shown in FIG. 6.

Methods and Material

T4 lysozyme was inserted in the second and third cytoplasmic loops of human GLP1R using standard molecular biology techniques. These constructs were transiently expressed from a modified pcDNA3.1 in HEK293T cells, generating receptors fused to EEGFP at their C-termini. Transfections were carried out using GeneJuice (Merck Biosciences) according to the manufacturer's guideline. Typically, 6 ug of DNA was used to transfect $3 \times 10^6$ adherent cells in 10 cm plates. Cells were harvested about 40 hours post transfection and re-suspended in 50 mM HEPES pH 7.5/150 mM NaCl/0.5 mM EDTA complemented with Complete EDTA-free protease inhibitor cocktail (Roche). Typically 650 ug of each sample was solubilised with 1% DDM in total volume of 200 uL for 1 hour at 4° C. followed by centrifugation at 50000 rpm for 30 minutes. 50 uL of the supernatant was loaded onto BioSEep-SEC-S3000 column (Phenomenex), pre-equilibrated with SEC buffer (50 mM HEPES pH 7.5/150 mM NaCl/0.5 mM EDTA/0.03% DDM) and run at the flow rate of 1 mL/minute for 15 minutes. The eluent was passed through an on-line fluorometer with the following settings: excitation 490 nm, emission 513 nm and gain of 13.

REFERENCES

[1] Kristiansen, K. Molecular mechanisms of ligand binding, signaling, and regulation within the superFamily of G-protein-coupled receptors: molecular modeling and mutagenesis approaches to receptor structure and function. *Pharma & Therap* 103, 21-80 (2004).

[2] Bill R M, Henderson P J, Iwata S, Kunji E R, Michel H, Neutze R, Newstead S, Poolman B, Tate C G and Vogel H. Overcoming barriers to membrane protein structure determination. *Nat Biotechnol*. 29(4), 335-340 (2011).

[3] Kobilka B K, Kobilka T S, Daniel K, Regan J W, Caron M G and Lefkowitz R J. Chimeric alpha 2-,beta 2-adrenergic receptors: delineation of domains involved in effector coupling and ligand binding specificity. *Science* 240 (4857) 1310-6 (1988).

[4] Frimurer T M and Bywater R P. Structure of the integral membrane domain of the GLP1 receptor. *Proteins* 35(4), 375-86 (1999).

[5] Kawate T and Gouaux E. Fluorescence-detection size-exclusion chromatography for precrystallization screening of integral membrane proteins. *Structure* 14(4), 673-81 (2004).

The invention claimed is:

1. A fusion protein comprising, from N-terminus to C-terminus:
   a) a first portion of a Family B G-protein coupled receptor (GPCR) that comprises transmembrane helix (TM)-1, TM2 and TM3 of the GPCR, wherein the TM1 and the TM2 are joined by intracellular loop 1 (ICL1), and the TM2 and TM3 are joined by extracellular loop 1 (ECL1);
   b) a polypeptide selected from the group consisting of a lysozyme, a cytochrome$_{b562}$, a flavodoxin, a β-lactamase, and a 70 kDa heat shock ATPase domain; and
   c) a second portion of the GPCR comprising TM4, TM5, TM6 and TM7 of the GPCR, wherein the TM4 and the TM5 are joined by extracellular loop 2 (ECL2), the TM5 and the TM6 are joined by intracellular loop 3 (ICL3), and the TM6 and the TM7 are joined by extracellular loop 3 (ECL3);
   wherein the polypeptide is inserted into the intracellular loop 2 (ICL2) region of the GPCR which loop joins the TM3 in the first portion of the GPCR and the TM4 in the second portion of the GPCR, and
   wherein the fusion protein displays reduced aggregation in the presence of a detergent solution, as compared to a GPCR without insertion of the polypeptide into the ICL2 region of the GPCR.

2. The fusion protein according to claim 1, wherein the polypeptide is inserted into the ICL2 region of the GPCR at a position between amino acid residues that correspond to amino acids Phe 257 and Ser 261 of human GLP1R, wherein Phe 257 corresponds to the fifth amino acid in SEQ ID NO: 30 and Ser 261 corresponds to the ninth amino acid in SEQ ID NO: 30.

3. The fusion protein according to claim 2, wherein the polypeptide is inserted into the ICL2 region of the GPCR after an amino acid corresponding to amino acid Phe 257 of human GLP1R and before an amino acid corresponding to amino acid Ser 261 or Phe 260 or Val 259, wherein Phe 257 corresponds to the fifth amino acid in SEQ ID NO: 30, Ser 261 corresponds to the ninth amino acid in SEQ ID NO:30, Phe 260 corresponds to the eighth amino acid in SEQ ID NO: 30, and Val 259 corresponds to the seventh amino acid in SEQ ID NO: 30.

4. The fusion protein according to claim 2, wherein the polypeptide is inserted into the ICL2 region of the GPCR after an amino acid corresponding to amino acid Ser 258 of human GLP1R and before an amino acid corresponding to amino acid Ser 261 or Phe 260 or Val 259 of human GLP1R, wherein Ser 258 corresponds to the sixth amino acid in SEQ ID NO: 30, Ser 261 corresponds to the ninth amino acid in SEQ ID NO: 30, Phe 260 corresponds to the eighth amino acid in SEQ ID NO: 30, and Val 259 corresponds to the seventh amino acid in SEQ ID NO: 30.

5. The fusion protein according to claim 1, wherein the polypeptide comprises lysozyme.

6. The fusion protein according to claim 1, further comprising a detectable moiety.

7. The fusion protein according to claim 6, wherein the detectable moiety is EGFP.

8. A crystal comprising the fusion protein of claim 1.

9. The fusion protein according to claim 1, which is in a solubilized form or which is substantially free of other proteins or which is immobilized to a solid support.

10. The fusion protein according to claim 1, wherein the Family B GPCR is a glucagon-like peptide 1 receptor (GLP1R), glucagon-like peptide 2 receptor (GLP2R), or glucagon receptor.

11. The fusion protein according to claim 1, wherein the Family B GPCR is a calcitonin receptor (CT).

12. The fusion protein according to claim 1, wherein the Family B GPCR is an amylin/CGRP receptor (AMY$_1\alpha$), amylin receptor (AMY$_2\alpha$), amylin/CGRP receptor (AMY$_3\alpha$), CGRP/adrenomedullin receptor (CGRP$_1\alpha$), adrenomedullin/CGRP receptor (AM$_1\alpha$), or adrenomedullin/CGRP receptor (AM$_2\alpha$ receptor).

13. The fusion protein according to claim 1, wherein the Family B GPCR is a corticotropin releasing factor receptor (CRF$_1$), or urocortins receptor (CRF$_2$).

14. The fusion protein according to claim 1, wherein the Family B GPCR is a growth hormone releasing hormone receptor (GHRH).

15. The fusion protein according to claim 1, wherein the Family B GPCR is a gastric inhibitory polypeptide receptor (GIP).

16. The fusion protein according to claim 1, wherein the Family B GPCR is a secretin receptor.

17. The fusion protein according to claim 1, wherein the Family B GPCR is a TIP-39 receptor (PTH2), or parathyroid hormone receptor (PTH1).

18. The fusion protein according to claim 1, wherein the Family B GPCR is a VIP/PACAP receptor (VPAC$_1$), PACAP receptor (PAC$_2$), or VIP/PACAP receptor (VPAC$_2$).

19. The fusion protein according to claim 1, wherein the polypeptide is a lysozyme and wherein the amino acid sequence of the lysozyme is at least 90% identical to SEQ ID NO: 24.

20. The fusion protein according to claim 5, wherein the lysozyme is T4 lysozyme.

21. The fusion protein according to claim 6, wherein the detectable moiety is a fluorescent label, a radiolabel, or an enzymatic label.

* * * * *